(12) United States Patent
Labaer et al.

(10) Patent No.: US 11,828,753 B2
(45) Date of Patent: *Nov. 28, 2023

(54) BIOSENSOR MICROARRAY COMPOSITIONS AND METHODS

(71) Applicant: Arizona Board of Regents on Behalf of Arizona State University, Scottsdale, AZ (US)

(72) Inventors: Joshua Labaer, Chandler, AZ (US); Bharath Takulapalli, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/201,742

(22) Filed: Mar. 15, 2021

(65) Prior Publication Data

US 2022/0042981 A1 Feb. 10, 2022

Related U.S. Application Data

(63) Continuation of application No. 14/776,163, filed as application No. PCT/US2014/028154 on Mar. 14, 2014, now Pat. No. 10,983,118.

(60) Provisional application No. 61/791,952, filed on Mar. 15, 2013.

(51) Int. Cl.
*G01N 33/543* (2006.01)

(52) U.S. Cl.
CPC ... *G01N 33/54373* (2013.01); *G01N 2440/00* (2013.01)

(58) Field of Classification Search
None
See application file for complete search history.

(56) References Cited

U.S. PATENT DOCUMENTS

| | | |
|---|---|---|
| 4,402,819 A | 9/1983 | Rechnitz |
| 4,596,772 A | 6/1986 | Kamei |
| 4,713,165 A | 12/1987 | Conover |
| 5,973,124 A | 10/1999 | Bayer |
| 6,309,842 B1 | 10/2001 | Dower |
| 6,565,813 B1 | 5/2003 | Garyantes |
| 6,570,158 B2 | 5/2003 | Feygin |
| 6,602,702 B1 | 8/2003 | McDevitt |
| 6,913,896 B1 | 7/2005 | Raven |
| 7,378,280 B2 | 5/2008 | Quake |
| 7,648,828 B2 | 1/2010 | Chan-Hui |
| 9,250,229 B2 | 2/2016 | Holmes |
| 9,523,688 B2 * | 12/2016 | Faure ............... C07K 14/4702 |
| 9,619,627 B2 | 4/2017 | Holmes |
| 10,983,118 B2 * | 4/2021 | Labaer ............ G01N 33/54373 |
| 2002/0058273 A1 | 5/2002 | Shipwash |
| 2002/0090649 A1 | 7/2002 | Chan |
| 2003/0017507 A1 | 1/2003 | Johnson |
| 2003/0113738 A1 | 6/2003 | Liu |
| 2003/0207290 A1 | 11/2003 | Kenten |
| 2004/0146516 A1 | 7/2004 | Roben |
| 2004/0157271 A1 | 8/2004 | Kirakossian |
| 2004/0161748 A1 | 8/2004 | He |
| 2004/0171034 A1 | 9/2004 | Agnew |
| 2005/0048580 A1 | 3/2005 | Labaer |
| 2005/0095661 A1 | 5/2005 | Hamon |
| 2010/0081132 A1 | 4/2010 | Horesh |
| 2010/0297250 A1 | 11/2010 | Boons |
| 2012/0208174 A1 | 8/2012 | Galush |
| 2013/0293884 A1 | 11/2013 | Lee |
| 2014/0106469 A1 | 4/2014 | Wu |
| 2014/0371091 A1 | 12/2014 | Wiktor |
| 2015/0211048 A1 | 7/2015 | Ramsey |
| 2015/0293089 A1 | 10/2015 | Araz |
| 2017/0138942 A1 | 5/2017 | Fan |

FOREIGN PATENT DOCUMENTS

| | | | |
|---|---|---|---|
| WO | 2005075996 A1 | 8/2005 | |
| WO | 2006014424 A2 | 2/2006 | |
| WO | 2006133476 A2 | 12/2006 | |
| WO | 2006013110 A1 | 2/2009 | |
| WO | 2010100265 A1 | 9/2010 | |
| WO | WO2011035177 * | 3/2011 | ............. G01N 33/50 |
| WO | 2013045700 A1 | 4/2013 | |
| WO | 2013174942 A1 | 11/2013 | |
| WO | 2013186359 A1 | 12/2013 | |
| WO | 2014143954 A2 | 9/2014 | |

OTHER PUBLICATIONS

Angenendt, P., et al. "Cell-free protein expression and functional assay in nanowell chip format." Analytical chemistry 76.7 (2004): 1844-1849.

Ariyasu, S. et al. Selective capture and collection of live target cells using a photoreactive silicon wafer device modified with antibodies via a photocleavable linker. Langmuir, 2012, 28(36): 13118-13126.

Assay designs for immobilization of his-tagged proteins. Dec. 14, 2010. [Retrieved from internet Mar. 17, 2016: http://www.siliconkinetics.com/pdf/Ski_Assay_Designs_for_Immobilization_AN13.pdf]: total pp. 4.

Berrade, Luis; Garcia, Angie E.; Camarero, Julio A. Protein Microarrays: Novel Developments and Applications. Pharm. Res., 2011, vol. 28(7): 1480-1499.

Boon, E.M., et al. An electrical probe of protein-DNA interactions on DNA-modified surfaces. Nat. Biotechnol., 2002, vol. 20(3): 282-286.

(Continued)

*Primary Examiner* — Ann Montgomery

(74) *Attorney, Agent, or Firm* — Quarles & Brady, LLP

(57) ABSTRACT

Described herein are biosensor microarrays comprising detector polypeptide monolayers substantially free of contaminants. Also provided are methods for generation of such biosensor microarrays by capture of polypeptides by arrays comprising capture moieties and associated sensors.

20 Claims, 19 Drawing Sheets

Specification includes a Sequence Listing.

(56) References Cited

OTHER PUBLICATIONS

Chandra, H. et al. "Cell-free synthesis-based protein microarrays and their applications." Proteomics 10.4 (2010): 717-730.
Funeriu, D.P., et al. Enzyme family-specific and activity-based screening of chemical libraries using enzyme microarrays. Nat. Biotechnol. 2005, 23(5): 622-627.
Gropeanu, M. et al. A versatile toolbox for multiplex protein micropatterning by laser lithography. Small, 2013, 9(6): 838-884.
Hirsch, J. D., et al. Easily reversible desthiobiotin binding to streptavidin, avidin, and other biotin-binding proteins: uses for protein labeling, detection, and isolation. Anal. Biochem. 2002, 308: 343-357.
International Search Report for PCT application No. PCT/US2014/028154 filed on Mar. 14, 2014.
Kyo, M., et al. "Label-free detection of proteins in crude cell lysate with antibody arrays by a surface plasmon resonance imaging technique." Analytical chemistry 77.22 (2005): 7115-7121.
Ladd, J., et al. "Label-free detection of cancer biomarker candidates using surface plasmon resonance imaging." Analytical and bioanalytical chemistry 393.4 (2009): 1157-1163.
Lee, H. J., et al. "Surface plasmon resonance imaging measurements of antibody arrays for the multiplexed detection of low molecular weight protein biomarkers." Analytical chemistry 78.18 (2006): 6504-6510.
Link, H., et al. Systematic identification of allosteric protein-metabolite interactions that control enzyme activity in vivo. Nature Biotechnology, 2013, 31(4): 357-361.
Macbeath, G and Schreiber, SL. Printing proteins as microarrays for high-throughput function determination. Science, 2000, vol. 289 (5485): 1760-1763.
Macbeath, G., et al. Printing Small Molecules as Microarrays and Detecting Protein-Ligand Interactions en Masse. J. Am. Chem. Soc. 1999, 121: 7967-7968.
Moth-Poulsen, K. et al. Optically induced linking of protein and nanoparticles to gold surfaces.Bioconjug Chem, 2010, 21(6): 1056-1061.
Samanta, D. et al. Immobilization of bio-macromolecules on self-assebled monolayers: methods and sensor applications. Chem Soc rev, 2011, 40(5): 2567-2592.
Seefeld, T.H., et al. On-chip synthesis of protein microarrays from DNA microarrays via coupled in vitro transcription and translation for surface plasmon resonance imaging biosensor applications. J. Am. Chem. Soc. 2012, 134(30): 12358-12361.
Stern, E., et al. Label-free biomarker detection from whole blood. Nat. Nanotechnol. 2010, 5(2): 138-142.
Takulapalli, B. R., et al. High Density Diffusion-Free Nanowell Arrays. J. Proteome Res. 2012, 11(8): 4382-4391.
Templin, M.F., et al. Protein microarray technology. Drug Discovery Today, 2002, vol. 7(15): 815-822.
Wang, W., et al. Label-free detection of small-molecule-protein interactions by using nanowire nanosensors. Proc. of nat. acad. sci., 2005 vol. 102(9):3208-3212.
Yang, M. et al. Bioactive surfaces prepared via the self-assembly of dendron thiols and subsequent dendrimer bridging reactions. Langmuir, 2005, 21(5): 1858-1865.

* cited by examiner

Figure 2
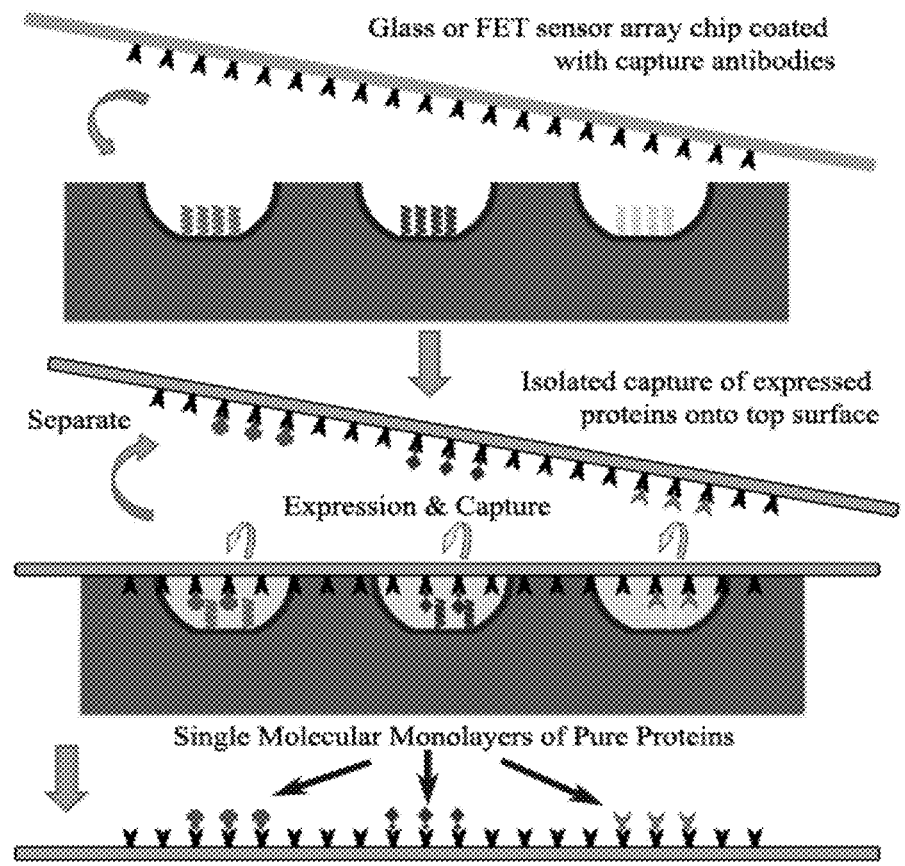
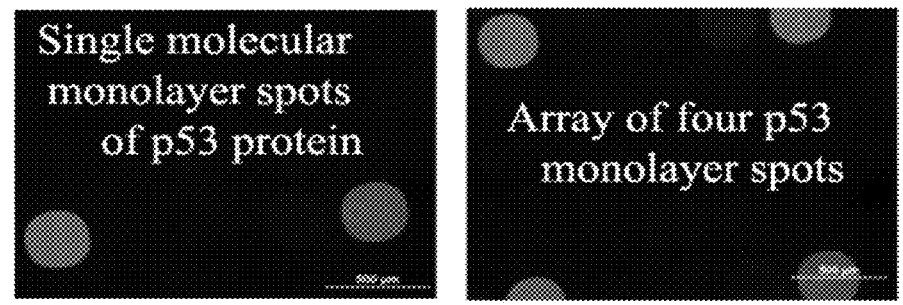

Real time detection of SRC auto-phosphorylation inhibition by Staurosporine drug molecule (2 µM)

Proteome biosensor chip

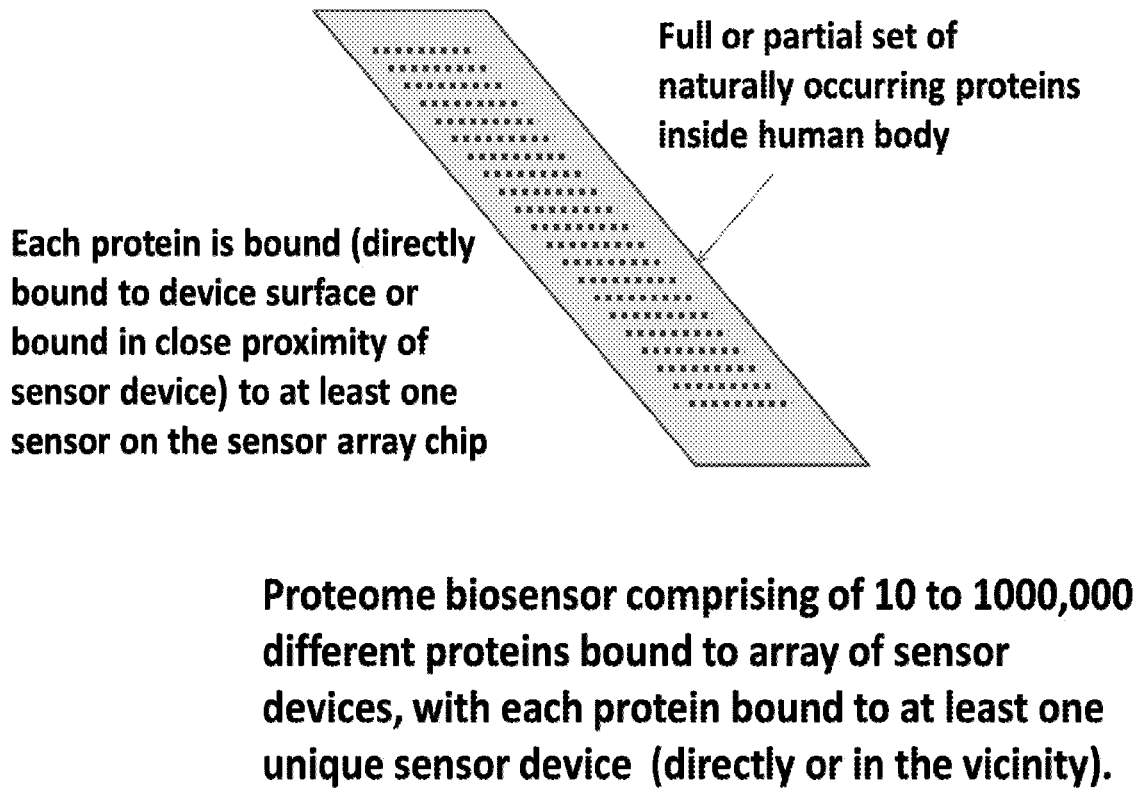

Each protein is bound (directly bound to device surface or bound in close proximity of sensor device) to at least one sensor on the sensor array chip Full or partial set of naturally occurring proteins inside human body Proteome biosensor comprising of 10 to 1000,000 different proteins bound to array of sensor devices, with each protein bound to at least one unique sensor device (directly or in the vicinity).

Figure 10

Example sensor array

Here nanowire sensors are shown as example, they can be substituted for any other sensors

Coat monolayers of tumor proteins, for example using IPC in-situ expression of tumor genes

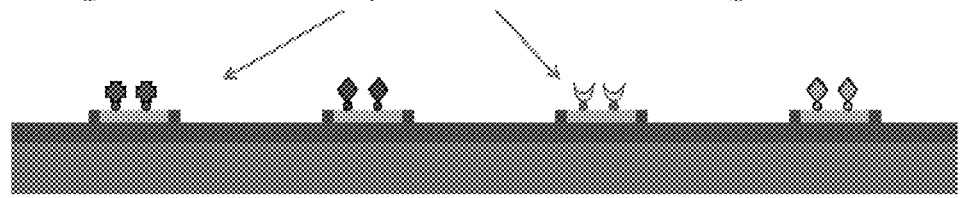

Test serum/blood/biopsy sample for specific antibodies

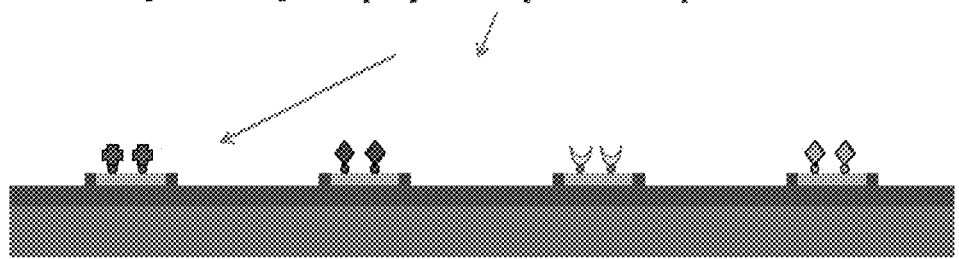

Antibody Signature detected from sensors in the array allows diagnosis & prognosis of the specific tumor/cancer

Antibody Profiling using Protein biosensors

Figure 11

Figure 13
Protease Enzymatic Activity
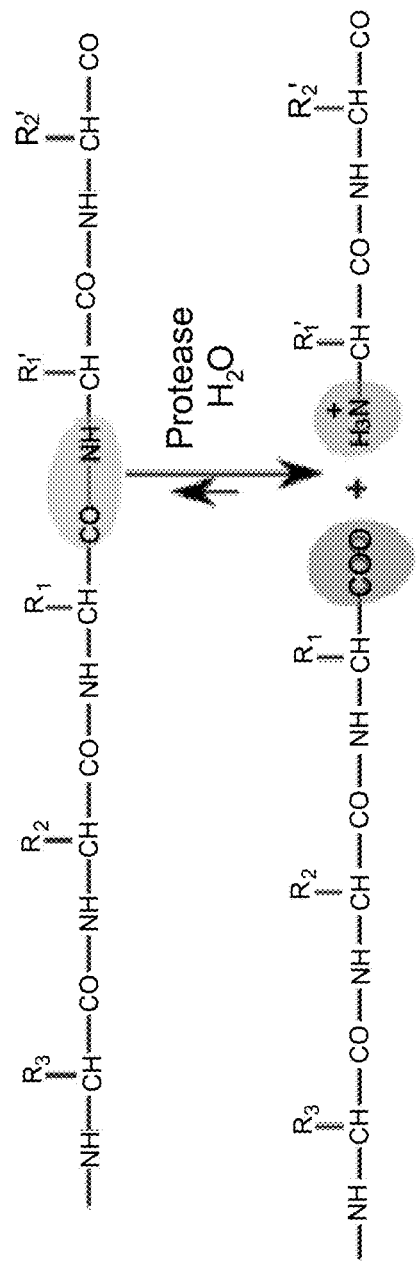
Oxidase Enzymatic Activity
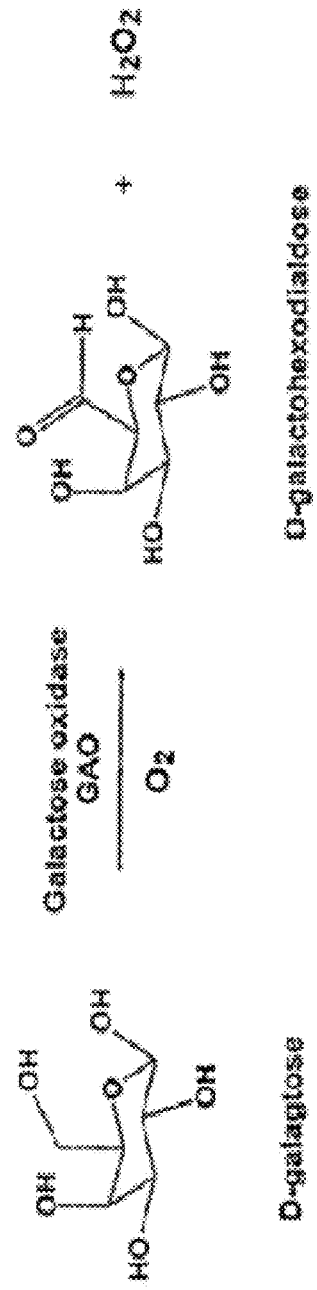

Ligase Enzymatic Activity
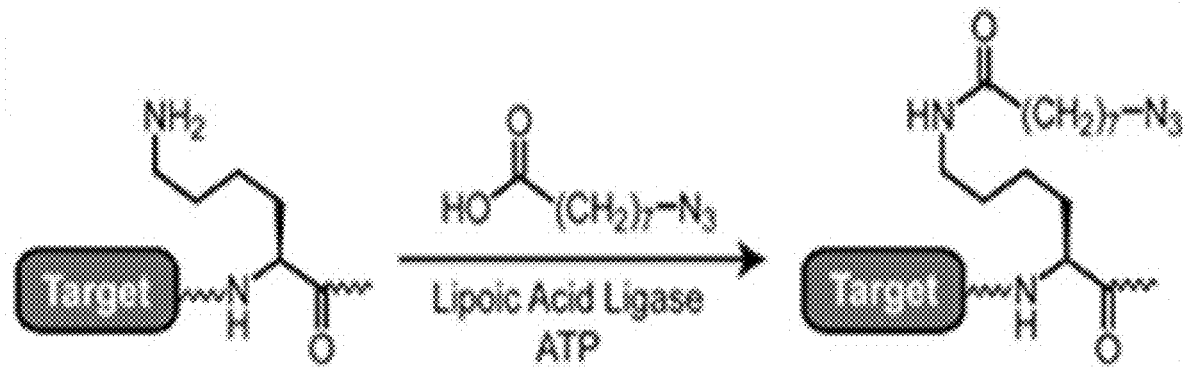
Detection of acetylcholinesterase interactions using electrode based sensors
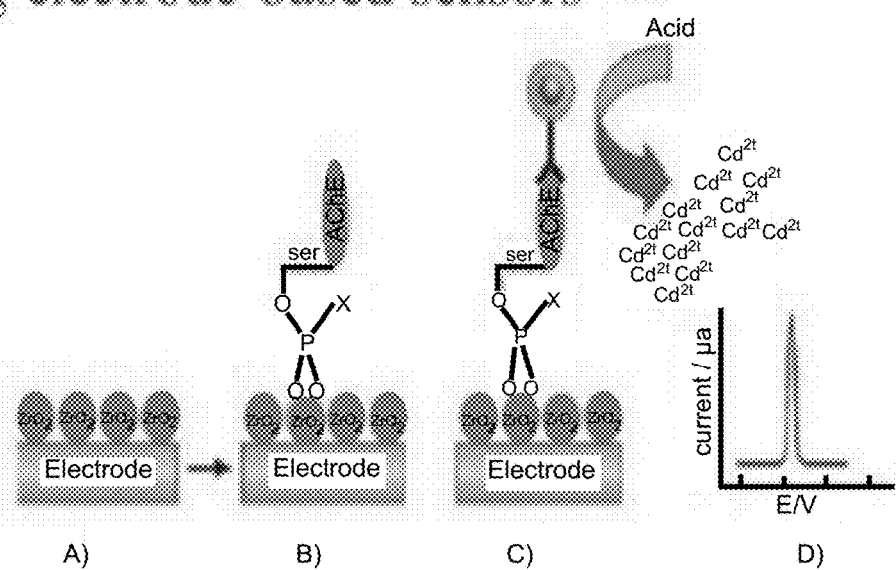
Figure: Example detection using an electrode
Figure 13 (continued)

Figure: Phosphorylation sensing using FET sensors

SEQUENCE LISTING

```
<160> NUMBER OF SEQ ID NOS: 1

<210> SEQ ID NO 1
<211> LENGTH: 297
<212> TYPE: PRT
<213> ORGANISM: Artificial Sequence
<220> FEATURE:
<223> OTHER INFORMATION: Recombinant protein derived from bacterial
      haloalkane dehalogenase

<400> SEQUENCE: 1

Met Ala Glu Ile Gly Thr Gly Phe Pro Phe Asp Pro His Tyr Val Glu
1               5                   10                  15
```

-continued

```
Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
            35                  40                  45

Arg Asn Ile Ile Pro His Val Ala Pro Thr His Arg Cys Ile Ala Pro
        50                  55                  60

Asp Leu Ile Gly Met Gly Lys Ser Asp Lys Pro Asp Leu Gly Tyr Phe
65                      70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
                100                 105                 110

Phe His Trp Ala Lys Arg Asn Pro Glu Arg Val Lys Gly Ile Ala Phe
            115                 120                 125

Met Glu Phe Ile Arg Pro Ile Pro Thr Trp Asp Glu Trp Pro Glu Phe
        130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
            195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
            245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
            275                 280                 285

Trp Leu Ser Thr Leu Glu Ile Ser Gly
290                 295
```

BIOSENSOR MICROARRAY COMPOSITIONS AND METHODS

CROSS REFERENCE

This application is a continuation of U.S. application Ser. No. 14/776,163, filed Sep. 14, 2015, which represents the national stage entry of PCT International Application No. PCT/US2014/028154, filed Mar. 14, 2014, and claims priority to U.S. provisional patent application Ser. No. 61/791,952, filed Mar. 15, 2013, the entire contents of which are incorporated by reference herein.

REFERENCE TO A SEQUENCE LISTING SUBMITTED VIA EFS-WEB

The content of the ASCII text file of the sequence listing named "112624_00628_ST25.txt" which is 2.98 kb in size was created on Mar. 3, 2021 and electronically submitted via EFS-Web herewith the application is incorporated herein by reference in its entirety.

BACKGROUND OF THE INVENTION

The current state of art in protein microarrays enables in situ production of high quality functional proteins from DNA microarrays in a high density format. Current methods/technologies include, for example, nucleic acid programmable protein array (NAPPA), Protein in situ array (PISA), In situ puromycin-capture, DNA array to protein array (DAPA), Nanowell protein arrays, Analytical microarrays (also known as capture arrays), Functional protein microarrays (also known as target protein arrays), Reverse phase protein microarray (RPPA) etc. In cell-free methods, micro arrays of coding cDNA, genes or plasmids are printed on a glass substrate and incubated with an in vitro transcription and translation (IVTT) mixture to express fresh proteins at the point of use. Protein arrays are also produced by printing prior-expressed purified proteins, but these often lose 3D-conformation dependent functionality during the laborious processes of expressing, isolating, purifying and printing. In-situ generated protein arrays are revolutionizing the field of proteomics by enabling high-throughput studies on proteins and protein-function for the first time. They are also finding wide use in biomarker discovery studies, discovering affinity binding agents, antibody profiling and clinical validation studies. Unfortunately, none of the current methods of producing protein arrays meet the challenges and quality demands for the generation of protein based biosensors.

SUMMARY OF THE INVENTION

Described herein are biosensor microarrays, methods for making such biosensor microarrays, and methods for their use.

In one aspect described herein is a biosensor microarray comprising: (i) a solid support substrate surface; (ii) a plurality of capture moeities linked to the solid support substrate surface; (iii) a plurality of detector polypeptides or detector peptides specifically bound by the capture moeities; and (iv) a plurality of sensors; wherein each sensor in the plurality of sensors is in direct contact or in proximity to a capture moiety in the plurality of capture moieties, and wherein biosensor microarray is substantially free of in vitro translation contaminants.

In some embodiments the detector polypeptides comprise kinases, proteases, phosphatases, oxidases, reductases, polymerases, hydrolases, lyases, transferases, isomerases, ligases, oxidoreductases, Glucosidases, Glycoside hydrolases, glycases. dehydrogenases, enolases, Secretases, synthases, Endonucleases, exonucleases, lipases, oxygenases, Cellulases, cyclases, esterases, or a combination thereof.

In some embodiments the detector polypeptides or detector peptides comprise are bound reversibly to the capture moieties. In some embodiments, where the detector polypeptides or peptides are bound reversibly to the capture moieties, the detector polypeptides or detector peptides further comprise a cleavable linker, wherein cleavage of the linker releases the detector polypeptides or detector peptides from the capture moieties. In some embodiments the cleavable linker is a protease-cleavable linker (e.g., a tobacco edge virus (TEV) protease cleavage site; an enterokinase cleavage site, a thrombin cleavage site, or an HRV3C protease cleavage site), a photocleavable linker, or a chemically reactive cleavable crosslinker). In some embodiments, where the detector polypeptides or peptides are bound reversibly, the capture moieties comprise non-covalent affinity moieties. In some embodiments, the detector polypeptides comprise the amino acid sequence of an avidin, and the non-covalent affinity moieties comprise desthiobiotin.

In some embodiments the capture moieties in the biosensor microarray comprise antibodies, biotin, or a ligand for a haloalkane dehalogenase tag polypeptide. In some embodiments the capture moieties are antibodies.

In some embodiments the plurality of capture moieties is linked to a plurality of beads or nanoparticles.

In some embodiments the detector polypeptides or detector peptides comprise at least one substrate to enzymatic post-translational modification (e.g., acylation, acetylation, de-acetylation, formylation, alkylation, methylation, amidation, glycosylation, oxidation, glycation, phosphorylation, biotinylation, ubiquitination, SUMOylation, Neddylation, sulfation, pegylation, citrullination, dephosphorylation, deamidation, or eliminylation).

In some embodiments, the plurality of detector polypeptides or detector peptides comprises at least two polypeptides or peptides comprising the same amino acid sequence, and one of the at least two polypeptides or peptides comprising the same amino acid sequence does not comprise the post-translational modification.

In some embodiments, where the capture moieties are antibodies, the detector polypeptides or detector peptides comprise an epitope tag and the antibodies bind specifically to the epitope tag. In some embodiments the epitope tag is glutathione-S transferase (GST), haloalkane dehalogenase, MYC-tag, FLAG-tag, hemagluttinin (HA) tag, a 6×-His tag, or a fluorescent protein.

In some embodiments the plurality of detector polypeptides or detector peptides comprise human polypeptides, viral polypeptides, bacterial polypeptides, fungal polypeptides, non-human animal polypeptides, plant polypeptides, or a combination thereof. In some embodiments the detector polypeptides or detector peptides comprise human polypeptides. In some embodiments the detector polypeptides or detector peptides comprise at least 100 separate human protein sequences (e.g., 1,000, 5,000, 10,000, or 20,000 human protein sequences). In some embodiments the human detector polypeptides or peptides c are cancer-associated polypeptides or peptides. In some embodiments the detector polypeptides are viral polypeptides, bacterial polypeptides, fungal polypeptides or a combination thereof.

In some embodiments the substrate surface of the biosensor microarray is gold, silver, germanium, alumina, or a sandwich of metal films.

In some embodiments the plurality of sensors comprises field effect sensors, piezoelectric sensors, acoustic wave sensors, resonators, or cantilever sensors. In some embodiments the field effect sensors comprise semiconductor nanowire sensors, metal nanowires, carbon nanotubes, nanowires, grapheme based devices, nano ribbon sensors, polymer sensors, resistive sensors, capacitive sensors, inductive sensors, giant magneto resistance sensors, or a combination thereof.

In other embodiments the plurality of sensors comprises plasmonic sensors, calorimetric sensors, potentiometric sensors, amperometric sensors, conductometric sensors, ion channel sensors, ion sensitive sensors, or impedance spectroscopy-based sensors.

In some embodiments the plurality of detector polypeptides comprises amino acid sequences of at least 100 different proteins.

In some embodiments multiple sensors in the plurality of sensors are in direct contact with or in proximity to each capture moiety in the plurality of capture moieties. In some embodiments the multiple sensors comprise sensors having different shapes, different sizes, different thickness, different surface structure, different surface chemistry, or different electrical characteristics. In some embodiments at least one of the multiple sensors is a reference sensor.

In some embodiments the plurality of sensors comprises a sensor surface that is nano-structured, nano-patterned, micro-structured, micro-patterned, meso-structured, meso-patterned, nano-porous, or micro-porous.

In a related aspect described herein is a biosensor microarray assay, comprising the steps of (i) contacting the above-described biosensor microarray with a sample comprising one or more analytes, wherein specific binding or interaction or reaction of at least one of the analytes to at least one of the bound detector polypeptides or detector peptides of the plurality of detector polypeptides or detector peptides in the biosensor microarray generates a detectable signal; and (ii) detecting and determining the signal level associated with binding or interaction of reaction of the at least one analyte with the at least one detector polypeptide or peptide.

In some embodiments of the method at least ten different analytes are detected in the sample. In some embodiments at least one of the analytes to be detected is a protein, an enzyme, an antibody, a non-peptide drug candidate, a metabolite, or a nucleic acid. In some embodiments the analytes comprise one or more antibodies to be detected. In some embodiments the sample is a biological sample from a human subject. In some embodiments, where the sample is a biological sample comprising antibodies from a human subject, the method further comprises indicating the presence or absence of a health condition based on the presence or level of one or more of the antibodies.

In other embodiments the one or more analytes comprise a drug candidate compound of molecular weight between about 100 daltons and about 900 daltons.

In other embodiments of the method one or more of the detector polypeptides or detector peptides are reversibly bound to the capture moieties. In some embodiments, where one or more of the detector polypeptides or detector peptides are reversibly bound to the capture moieties, the method further comprises releasing the reversibly bound detector polypeptides or peptides prior to contacting the biosensor microarray with the sample.

In another aspect described herein is a biosensor microarray comprising: (i) a solid support substrate surface; (ii) a plurality of capture moieties linked to the solid support substrate surface; (iii) a plurality of reactive polypeptides bound by the capture moieties, wherein each bound reactive polypeptide has an activity that interacts or reacts in the presence of a target ligand to generate a reporter agent; and (iv) a plurality of sensors that generate a detectable signal in the presence of the target ligand or the reporter agent; wherein each sensor in the plurality of sensors is in direct contact with or in proximity to a capture moiety in the plurality of capture moieties, and wherein the biosensor microarray is substantially free of in vitro translation contaminants.

In some embodiments the plurality of sensors are located on a solid support substrate surface other than the solid support substrate to which the plurality of capture moieties is linked.

In some embodiments, the reporter agent generated by the reactive polypeptide is non-fluorescent. In other embodiments the ligand or reporter agent is a reactive or redox species that generates a detectable electrical charge transfer. In some embodiments the reporter agent is a reporter polypeptide. In some embodiments the reporter polypeptide is a polypeptide that is post-translationally modified by one or more reactive polypeptides in the plurality of reactive polypeptides.

In further embodiments the biosensor microarray further comprises a plurality of capture moieties that bind specifically to the reporter agent.

In other embodiments the plurality of sensors further comprise a coated layer that is sensitive to the presence of the reporter agent. In some embodiments the coated layer comprises an organic monolayer, a biomolecular monolayer, an inorganic monolayer, a multi layer film, a metal film, a dielectric film, or a semiconducting film.

In other embodiments the ligand or the reporter agent reacts with another chemical or biological monolayer or multilayer or film or organic or inorganic or dielectric or metal or insulator or topological insulator or semiconductor film deposited on sensor surface, causing a response in the sensor.

In a related aspect described herein is a biosensor microarray assay comprising: (i) contacting the just-mentioned biosensor microarray with a test sample comprising one or more target ligands, whereby reaction of the one or more target ligands with one or more of the reactive polypeptides generates a reporter agent(s); and (ii) detecting and determining the signal level of the reporter agent(s).

In a further aspect provided herein is a method for generating a biosensor microarray, comprising: (i) providing a plurality of capture moieties; linked to a solid support substrate surface, wherein a plurality of sensors are in direct contact or in proximity to the plurality of capture moieties; (ii) providing arrayed in vitro translation reactions comprising RNAs encoding diverse detector polypeptides, ribosomes, and diverse detector polypeptides translated from the RNAs; (iii) contacting the arrayed in vitro translation reactions with the plurality of capture moieties, whereby the diverse detector polypeptides bind specifically to the array of capture moieties; and (iv) washing the contacted capture moieties to remove in vitro translation contaminants that are non-specifically bound to the capture moieties, whereby a biosensor microarray substantially free of in vitro translation contaminants is obtained.

In some embodiments of the just described method, the plurality of in vitro translation reactions comprises at least 100 (e.g., 500, 1,000, 5,000, or 10,000) in vitro translation reactions, wherein each in vitro translation reaction comprises a translated detector polypeptide with a different amino acid sequence from the amino acid sequences of the other translated detector polypeptides.

In some embodiments the arrayed in vitro translation reactions are arrayed in microwells or nanowells.

In some embodiments the plurality of sensors in the biosensor microarray to be generated comprises field effect transistor (FET) sensors.

BRIEF DESCRIPTION OF THE DRAWINGS

FIG. 2 (top panel) shows a schematic illustration of isolated capture of expressed proteins using a sensor array chip coated with capture antibodies. The antibody-coated sensor array is brought into contact with various proteins generated by in vitro translation reactions resulting in the translated target proteins binding to their corresponding antibody to yield a monolayer array of captured/isolated proteins. (bottom panel) Fluorescence micrograph of purified p53 monolayer spots in an array.

FIG. 10 shows a schematic illustration of a non-limiting embodiment of a proteome biosensor chip in which a full set or subset of human proteins is bound on the surface of a sensor array (e.g., a nanowire sensor array), where each protein is bound directly or in close proximity to a separately addressable sensor device.

FIG. 11 shows a schematic illustration of a non-limiting embodiment of a nanowire sensor-based biosensor microarray. Isolated protein capture is used to capture expression products of tumor genes on nanowire sensor surface. Subsequently biological samples (e.g., serum or whole blood) can be analyzed for the presence and quantity of specific antibodies based on their specific interactions with their target protein antigens bound on the nanowire sensor surface. The signalling pattern thereby yields an antibody profiling signature associated with the diagnosis or prognosis with a specific tumor/cancer type.

DETAILED DESCRIPTION OF THE INVENTION

Introduction

Figure 1:
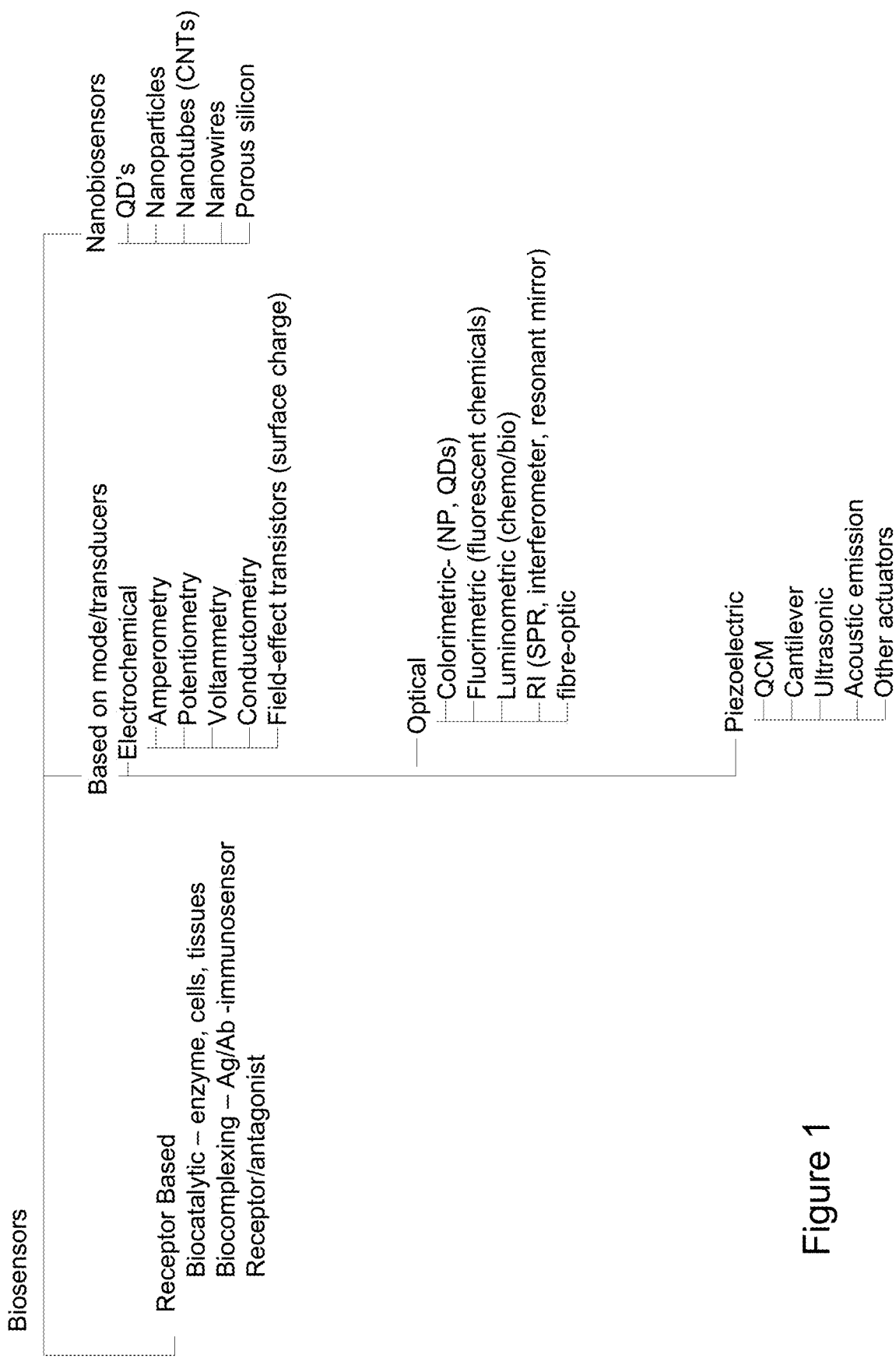
FIG. 1 shows a schematic overview of various classes of biosensors and their detection modalities.

To date, while it has been possible to coat a limited array of sensors with monolayers of pure proteins previously expressed and purified, it is not possible to do this for large array of sensors with tens of thousands of proteins without a loss of protein functionality. Current protein-based biosensors use a small array of sensor devices coated with a limited set of predetermined proteins (or other biomolecules) to detect pre-identified biomarker(s) of interest, to diagnose a disease. As exemplified by the current controversy over utility of PSA tests, diagnosis of disease based on over-expression or under-expression of a single biomarker (or even a small panel of biomarkers) may lead to sub-optimal decisions in a significant number of cases. Rather than detecting regulation of a single protein (or its antibody), a more optimum method is to get a snap shot of expression levels of many tissue-specific proteins, or antibodies. A disease signature approach to diagnosing health conditions, enabled by the biosensor microarrays and methods described herein, involves detecting a large number of binding or interacting or reacting species, minimizing errors such as over or under diagnosis. Hence, one of the biggest challenges in biosensors field is to produce a large array of sensors (100 sensors up-to up-to 10,000,000 sensor units or more), each sensor coated with a monolayer of detector polypeptides capable of interacting with analytes of interest (e.g., other proteins, enzymes, antibodies, metabolites, nucleic acids or small molecule drugs).

In current methods nucleic acids (e.g., plasmid DNA and/or mRNAs) and capture agents for expression products are printed together along with ribosomes and other components needed for in vitro translation. Thus the biomolecules that are produced in-situ from DNA, the expression products (i.e., translated polypeptides or peptides) are captured on and around the printed mass of materials. When such an array is exposed to test medium for application as a biosensor, the "target species may interact nonspecifically" i.e. bind or interact or react non-specifically to the secondary materials present in the printed mass, which, in effect, are "contaminants" from in vitro translation reactions, e.g., ribosomes, amino acids, tRNAs, mRNAs, DNA, organic molecules etc. Alternately, these in vitro translation contaminants may bind or interact (nonspecifically) with non-target molecules and materials present in the test solution (analyte). These undesired secondary interactions add to the noise, and reduce specificity of detection by lowering signal to noise ratio in detecting the target biomolecular species. What is ideally desired for biosensors is presence of only pure detector polypeptides (pure biomolecules) of interest on the surface (or in the vicinity) of the signal transducing element, along with only the required components such as reactant chemicals, biomolecules or catalysts or enzymes.

The ability of bio-sensors or signal transducers to detect a target species of interest depends on the amplitude of signal (or change in signal) produced by the sensing event. And often times in biosensors, the efficiency or amplitude of signal transduction is directly proportional to 'physical/electronic proximity' of the binding/interacting event to the sensitive transducing element'. The change in the electric or electrochemical or magnetic or optical or thermal properties of the signal transducing element is a maximum when the binding or interacting event occurs closest to the sensing element. Current protein arrays that are formed on top of a crust of printed (dispensed) materials "screen" the signal sensitive element from the binding/interaction event, effectively reducing the sensitivity of detection by up-to an order of magnitude or more, rendering them less useful as sensors in most configurations (except using optical tags). Thus not only is the noise high, but also the signal itself is quite low—when current methods of protein production are used for biosensor applications. What is ideally desired for biosensors is a single monolayer or few multilayers or films of proteins (or other biomolecules of interest) directly attached to the surface (or in proximity) of the sensing element (or multi-layers where monolayer is not possible) as described herein.

Compositions
Biosensor Microarrays

A biosensor is a device that combines a signal transducing (sensing) element with a thin film or chemical or a biological component (biomolecule) to detect, quantify the presence or absence of specific chemical or biomolecular species of interest in a test medium via specific binding, interaction or biochemical reaction. Biosensor microarrays are arrays of sensors comprising a unique chemical or biological molecule on each (or multiple) of the sensor units, to combinatorially detect presence or absence of single or multiple biomolecules of interest in a test medium. The signal transducing element can comprise of an optically active tag such as a dye, quantum dot, magnetic particle, nanoparticle, or a radiometric tag. Biosensors can also comprise a sensor device that monitors changes produced in electrical properties such as resistive, capacitive, inductive, or mass, electrochemical, plasmonic or magnetic or optical or thermal (or a combination of these) properties of the transducing (sensing) element to detect target chemical or biomolecule of interest. Examples include field effect transistor (FET) nanowire sensors, ion sensitive FETs (ISFETS), SPR sensors, plasmonic sensors, quartz crystal microbalance etc. Current protein microarray technologies when applied to biosensor applications suffer from many limitations, as discussed below, issues such as low specificity resulting in high false positives, false negatives, and low sensitivity, low signal to noise ratios etc, which are avoided or reduced in the biosensor microarrays described herein.

In some embodiments, a biosensor microarray generated by the methods described herein comprises (i) a solid support substrate surface; (ii) a plurality of capture moieties linked to the solid support substrate surface; (iii) a plurality of detector polypeptides or detector peptides specifically bound by the capture moieties; and (iv) a plurality of sensors; wherein each sensor in the plurality of sensors is in direct contact or in proximity to a capture moiety in the plurality of capture moieties, and wherein biosensor microarray is substantially free of in vitro translation contaminants (i.e., in vitro translation reagents other than the translated detector polypeptides). In such embodiments the sensors detect to binding or interaction of target analytes detector polypeptides bound to the capture moieties.

Figure 8:
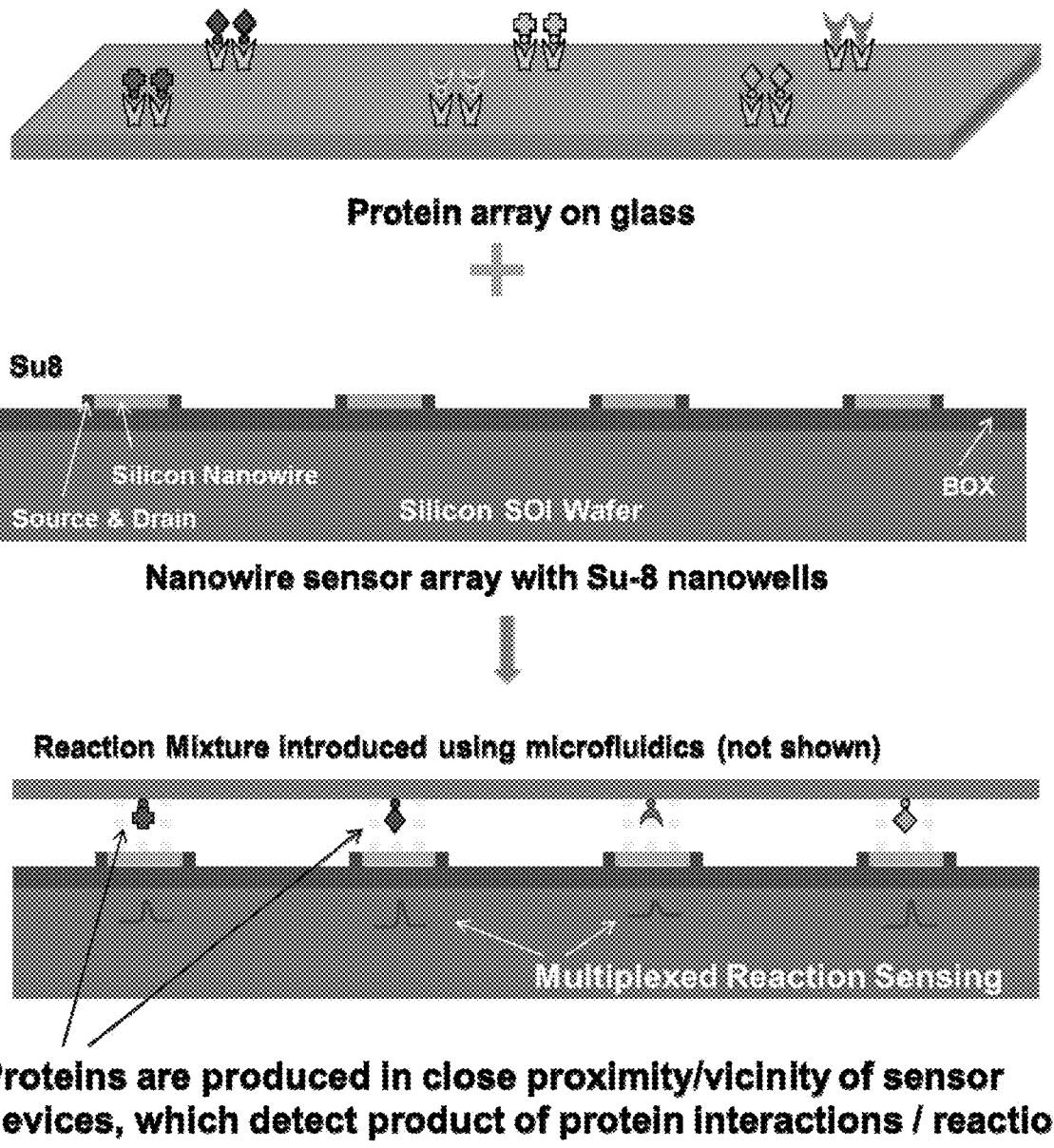

In other embodiments the biosensor microarray comprises: (i) a solid support substrate surface; (ii) a plurality of capture moieties linked to the solid support substrate surface; (iii) a plurality of reactive polypeptides bound by the capture moieties, wherein each bound reactive polypeptide (e.g., a kinase, a phosphatase, a protease, enzyme, or enzyme substrate) has an activity that interacts or reacts in the presence of a target ligand to generate a reporter agent; and (iv) a plurality of sensors that generate a detectable signal in the presence of the reporter agent; wherein each sensor in the plurality of sensors is in direct contact or in proximity to a capture moiety in the plurality of capture moieties, and wherein biosensor microarray is substantially free of in vitro translation contaminants. In such embodiments, a signal is generated indirectly by the generation of a reporter agent following interaction of a target ligand with a reactive polypeptide. The reporter agent, in some cases, can be a polypeptide (i.e., a "reporter polypeptide"). In some embodiments, the reporter polypeptide can be derived from a reactive polypeptide after it interacts with a target ligand (e.g., a kinase or protease). In some embodiments, where the biosensor microarray is configured to detect a reporter agent, the plurality of sensors are located on a solid support substrate surface other than the solid support substrate to which the plurality of capture moieties is linked, as illustrated in FIG. 8. In some embodiments, generation of a reporter agent requires contact of the target ligand and reactive polypeptide with other reagents that promote a reaction or interaction between the target ligand and reactive polypeptide (e.g., ATP or other metabolites)

Suitable solid support substrate surfaces include, but are not limited to, films of gold, silver, germanium, alumina, or a sandwich of metal films.

Suitable types of detector polypeptides include, but are not limited to, enzymes such as kinases, proteases, phosphatases, oxidases, reductases, polymerases, hydrolases, lyases, transferases, isomerases, ligases, oxidoreductases, Glucosidases, Glycoside hydrolases, glycases, dehydrogenases, enolases, Secretases, synthases, Endonucleases, exonucleases, lipases, oxygenases, cellulases, cyclases, and esterases.

In some embodiments the detector polypeptides in the biosensor microarray are reversibly bound to the capture moieties. For example, in embodiments where the detector polypeptides are reversibly bound, such detector polypeptides may include a cleavable linker, which allows release of a reversibly bound detector polypeptide to be released following cleavage of the linker. Examples of cleavable linkers include, but are not limited to, protease cleavable linkers, photocleavable linkers, and chemically reactive cleavable crosslinkers. Suitable protease cleavable linkers include, but are not limited to, protease recognition sites for tobacco edge virus (TEV) protease cleavage site; an enterokinase cleavage site, a thrombin cleavage site, and an HRV3C protease cleavage site. Photocleavable linkers can include photocleavable biotin (e.g., commercially available from Ambergen, Watertown, MA); 3-amino-3-(2-nitrophenyl)propionic acid (ANP; Ariyasu et al 2012, *Langmuir,* 28(36):13118-13126); and photocleavable histidine peptides (Gropeanu et al 2013, *Small.,* 9(6):838-884). Chemically reactive cleavable crosslinkers include, but are not limited to, thiol-cleavable crosslinkers (e.g., Dithiobis [succinimidyl propionate).

In some embodiments at least some of the capture moieties in a biosensor microarray are non-covalent affinity moieties, which allow non-covalent binding of a capture moiety with a detector polypeptide. For example, in some cases detector polypeptides are fusion polypeptides that comprise the amino acid sequence of an avidin (e.g., GenBank Accession No. CAC34569.1) at the —N or —C terminus and the non-covalent affinity moiety is desthiobiotin, which, while having high affinity for the avidin tag, is reversible in the presence of excess biotin which can competitively disrupt binding of the substrate-bound desthiobiotin (i.e., the capture moiety) to the avidin-bearing detector polypeptide.

Biosensor microarrays comprising reversibly bound detector polypeptides, detector peptides, or reactive polypeptides are particularly useful in some applications, as described herein, where the bound polypeptides are released (e.g., by protease cleavage, photolysis, or competitive binding of biotin) into solution into respective micro-wells or nanowells produced on the array prior to assaying of a sample for the presence of an analyte of interest.

Suitable capture moieties include, but are not limited to, antibodies, chemical linkers, affinity agents, biotin, avidin, or a ligand for a haloalkane dehalogenase tag polypeptide (a "halotag ligand") as described herein. In some embodiments, the plurality of detector polypeptides comprise fusion polypeptides, where the plurality of fusion polypeptides comprise diverse amino acid sequences and an N-terminal or C-terminal epitope tag amino acid sequence that is common to the plurality of detector polypeptides. In some embodiments, the capture moieties comprise antibodies. In some embodiments, the detector polypeptides or detector peptides comprise an epitope tag and the antibodies bind specifically to the epitope tag. In some embodiments, the epitope tag is glutathione-S transferase (GST), haloalkane dehalogenase, MYC-tag, FLAG-tag, hemagluttinin (HA) tag, a 6×-His tag, a fluorescent protein (e.g., EGFP). These epitope tags and specific antibodies or affinity reagents (e.g., chelated nickel) for such epitope tags are known in the art and commercially available from multiple sources.

In other embodiments, where the capture moieties are antibodies, the antibodies specific and directed to diverse detector polypeptide amino acid sequences in the plurality of detector polypeptides rather than to a common epitope tag.

In some embodiments the epitope tag (located on the N or C terminus of a fusion detector polypeptide) comprises the amino acid sequence of a haloalkane dehalogenase ("HaloTag®):

```
(HaloTagR® Amino Acid Sequence)
                                       SEQ ID NO: 1
MAEIGTGFPFDPHYVEVLGERMHYVDVGPRDGTPVLFLHGNPTSSYVWRN

IIPHVAPTHRCIAPDLIGMGKSDKPDLGYFFDDHVRFMDAFIEALGLEEV

VLVIHDWGSALGFHWAKRNPERVKGIAFMEFIRPIPTWDEWPEFARETFQ

AFRTTDVGRKLIIDQNVFIEGTLPMGVVRPLTEVEMDHYREPFLNPVDRE

PLWRFPNELPIAGEPANIVALVEEYMDWLHQSPVPKLLFWGTPGVLIPPA

EAARLAKSLPNCKAVDIGPGLNLLQEDNPDLIGSEIARWLSTLEISG
```

Where the detector polypeptides are fusion polypeptides comprising a HaloTag® epitope tag, the plurality of capture moieties comprise a HaloTag ligand comprising the structure of Formula I shown below:

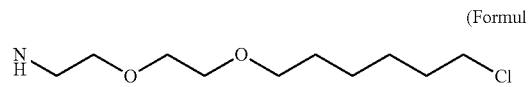

(Formula I)

Typically capture moieties are assembled as a monolayer on the solid support substrate surface, which has been derivatized to link to the capture moieties. Methods for derivatizing various types of substrate surfaces to allow linkage of biolmolecules is known in the art. See, e.g., Samanta et al (2011), *Chem Soc Rev.,* 40(5):2567-2592. Formation of an array pattern is then established by capture of detector polypeptides from arrayed in vitro translation reactions as described herein. In other embodiments the capture moieties themselves may be linked to a substrate surface as an array, e.g., by spotting in a grid pattern using a pin spotting device, or dispensed using liquid jet printers, or using vapor coating of chemical linkers.

Figure 9:
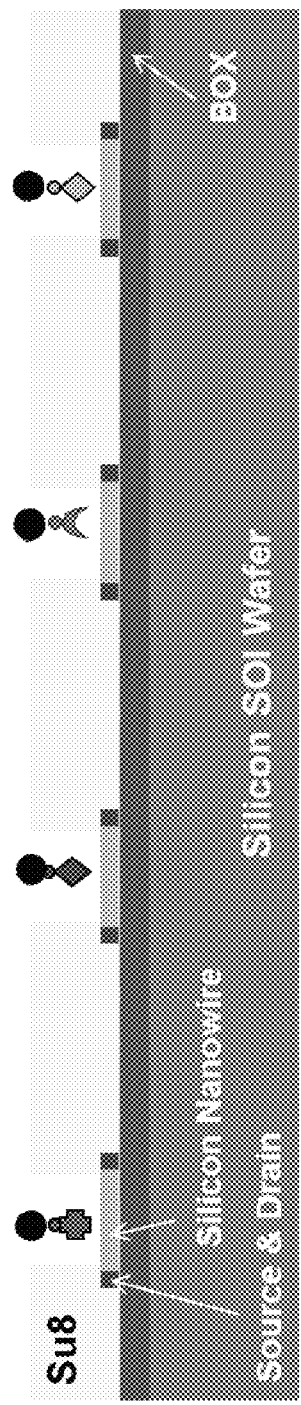
FIG. 9 shows a schematic illustration of a non-limiting embodiment of proximity protein sensing in which proteins are captured on beads and contacted with reactive substrates in close proximity to nanowire sensors.

In other embodiments the plurality of capture moieties is linked to a plurality of beads or nanoparticles, where different sets of nanoparticles are separately associated with different detector polypeptides rather than being confined to a two dimensional surface array. See, e.g., FIG. 9.

An advantage of the biosensor microarrays described herein is the large number of diverse detector polypeptides that can be represented. In some embodiments the plurality of detector polypeptides comprises amino acid sequences of at least 100 to about 100,000 different proteins, e.g., 200 proteins, 300 proteins, 400 proteins, 500 proteins, 1,000 proteins, 2,000 proteins, 3,000 proteins, 5,0000 proteins, 7,000 proteins, 8,000 proteins, 20,000, 30,000, 40,000, 50,000, 60,000, 70,000, 80,000, 90,000 or another number of proteins from at least 100 proteins to about 100,000 proteins. In other embodiments, the plurality of detector polypeptides comprises amino acid sequences of at least 3 proteins to about 50 different proteins, e.g., 5 proteins, 8 proteins, 10 proteins, 15 proteins, 20 proteins, 30 proteins, 40 proteins, or another number of proteins from at least 3 proteins to about 50 proteins. In some embodiments at least one of the detector polypeptides or detector peptides in the biosensor microarray comprises at least one substrate for post-translational modification, which undergoes enzymatic post translation modification reaction in presence of enzymes or enzymes and cofactors (e.g., enzymes found in a biological sample such as a blood or urine sample), which can be detected by the sensors. In some embodiments, the post-translational modification comprises acylation, acetylation, de-acetylation, formylation, alkylation, methylation, amidation, glycosylation, oxidation, glycation, phosphorylation, biotinylation, ubiquitination, SUMOylation, Neddylation, sulfation, pegylation, citrullination, dephosphorylation, deamidation, or eliminylation.

In some embodiments the plurality of detector polypeptides or detector peptides comprises at least two polypeptides or peptides comprising the same amino acid sequence, where one of the at least two polypeptides or peptides does not comprise the post-translational modification. This is useful, e.g., to detect protein-protein interactions that are dependent on a specific post-translational modification of one of the binding partners.

The amino acid sequences of the various detector polypeptides or detector peptides in the biosensor microarray correspond to amino acid sequences from a number of sources. In some embodiments the plurality of detector polypeptides or detector peptides comprise human polypeptides, viral polypeptides, bacterial polypeptides, fungal polypeptides, animal polypeptides, plant polypeptides, or a combination thereof. In some embodiments the detector polypeptides comprise human polypeptides, e.g., human polypeptides associated with a health condition including, but not limited to, cancers, pulmonary hypertension, diabetes, Alzheimer's, Parkinson's, CNS diseases, macular degeneration, Idiopathic pulmonary fibrosis, systemic sclerosis, and rheumatoid disorders. In some embodiments the detector polypeptides or peptides are cancer-associated polypeptides (e.g., p53, tumor antigens, or cancer cell line antigens).

In some embodiments, where the detector polypeptides are human polypeptides, the detector polypeptides comprise at least 1% to about 100% of human proteome sequences, e.g., 2%, 5%, 10%, 12%, 15%, 20%, 30%, 40%, 50%, 60%, 75%, 80%, 90%, or another percentage of human proteome sequences from at least 1% to about 100% of human proteome sequence. In some embodiments, the plurality of detector polypeptides comprise at least 10 to 500 separate human protein sequences, e.g., 50, 100, 200, 300, 400, or another number of human protein sequences from at least 10 to 500. In other embodiments, the detector polypeptides comprise at least 500 to about 50,000 separate human protein sequences or variants thereof having at least about 90% (e.g., 95%, 97%, 99%) sequence identity to the naturally occurring human protein sequences, e.g., at least 1,000, 2,000, 5,000, 10,000, 20,000, 30,000, 40,000 human protein sequences or another number of human protein sequences or variants thereof from at least 1,000 to about 50,000. See, e.g., FIG. 10.

In some embodiments the detector polypeptides in the biosensor microarray are viral polypeptides, bacterial polypeptides, fungal polypeptides or a combination thereof. Such arrays are useful, e.g., for detecting the presence of antibodies against viral pathogens (e.g., HIV) or bacterial pathogens (e.g., *Mycobacterium tuberculosis*).

Multiple types of sensors can be utilized in the biosensor microarrays described herein. In some embodiments the plurality of sensors comprise field effect sensors, piezoelectric sensors, acoustic wave sensors, plasmonic sensors, raman sensors, resonators, or cantilever sensors. In some embodiment the field effect sensors comprise semiconductor nanowire sensors, metal nanowires, carbon nanotubes, nanowires, grapheme based devices, nano ribbon sensors, polymer sensors, resistive sensors, capacitative sensors, inductive sensors, giant magneto resistance sensors, or a combination thereof.

In other embodiments the plurality of sensors in the biosensor microarray comprises calorimetric sensors, potentiometric sensors, amperometric sensors, conductometric sensors, ion channel sensors, ion sensitive sensors, impedance spectroscopy-based sensors, or surface-plasmon-polaritron sensors.

In some embodiments the plurality of sensors comprises surface enhanced raman spectroscopy (SERS) sensors. In other embodiments the plurality of sensors comprises SPM, AFM, STM-based sensors.

In some embodiments the sensors in the plurality of sensors comprise a plasmonic-active surface such as gold or silver film, or a sandwich of metal films, either continuous or in discrete micro, nano sized shapes, supported on a dielectric film or a glass or other surface.

In some embodiments a biosensor microarray may be configured such that there are multiple sensors in direct contact with or in proximity to each capture moiety, i.e., the ratio of sensors to capture moieties can be greater than 1:1, e.g., it can be 2:1 to about 100:1, e.g., 3:1, 5:1, 10:1, 20:1, 50:1, 75:1, or another ratio from 2:1 to about 100:1. In some embodiments the multiple sensors associated with a capture moiety comprise sensors having different shapes, different sizes, different thickness, different surface structure, different surface chemistry, or different electrical characteristics. In some embodiments at least one of the sensors associated with a capture moiety serves as a reference sensor, i.e., a sensor that differs in reactivity or sensitivity to reporter agents or the presence of analytes relative to other sensors.

In some embodiments the plurality of sensors includes sensors having a surface that is nano-structured, nano-patterned, micro-structured, micro-patterned, meso-structured, meso-patterned, nano-porous, or micro-porous.

In various embodiments, sensors are at a distance from their respective detector polypeptides ranging from at least 1 nm to about 1 mm, e.g., 10 nm, 100 nm, 1000 nm, 10,000 nm, 100,000 nm, or 500,000 nm, or another distance ranging from at least 1 nm to about 1 mm, depending on the particular detection modality. For example, typically the distance between the location of a detector polypeptide and a sensor can be longer when the analyte is a target ligand to be detected indirectly via the generation of a diffusible reporter agent as described herein.

The above-described biosensor microarray can detect the presence of an analyte, e.g., a polypeptide, a low molecular weight drug, or a carbohydrate by direct interaction between detector polypeptides and the analyte of interest. Alternatively, analytes can be detected indirectly by the generation of a byproduct or "reporter agent," resulting from the interaction of a detector polypeptide and a target ligand.

In some embodiments, where a biosensor microarray is sensitive to a reporter agent, the reporter agent is non-fluorescent. In some embodiments the reporter agent is a reactive or redox or charged or polarized or magnetic species that generates a detectable electrical charge transfer. In some embodiments the reporter agent is a reporter polypeptide. In some embodiments the reporter polypeptide is a polypeptide that is post-translationally modified by one or more reactive polypeptides in the plurality of reactive polypeptides. In some embodiments, a reactive polypeptide serves as a substrate (e.g., a protein kinase substrate) for a target ligand (e.g., a protein kinase), and following reaction with the target ligand itself becomes the reporter polypeptide.

Figure 13:
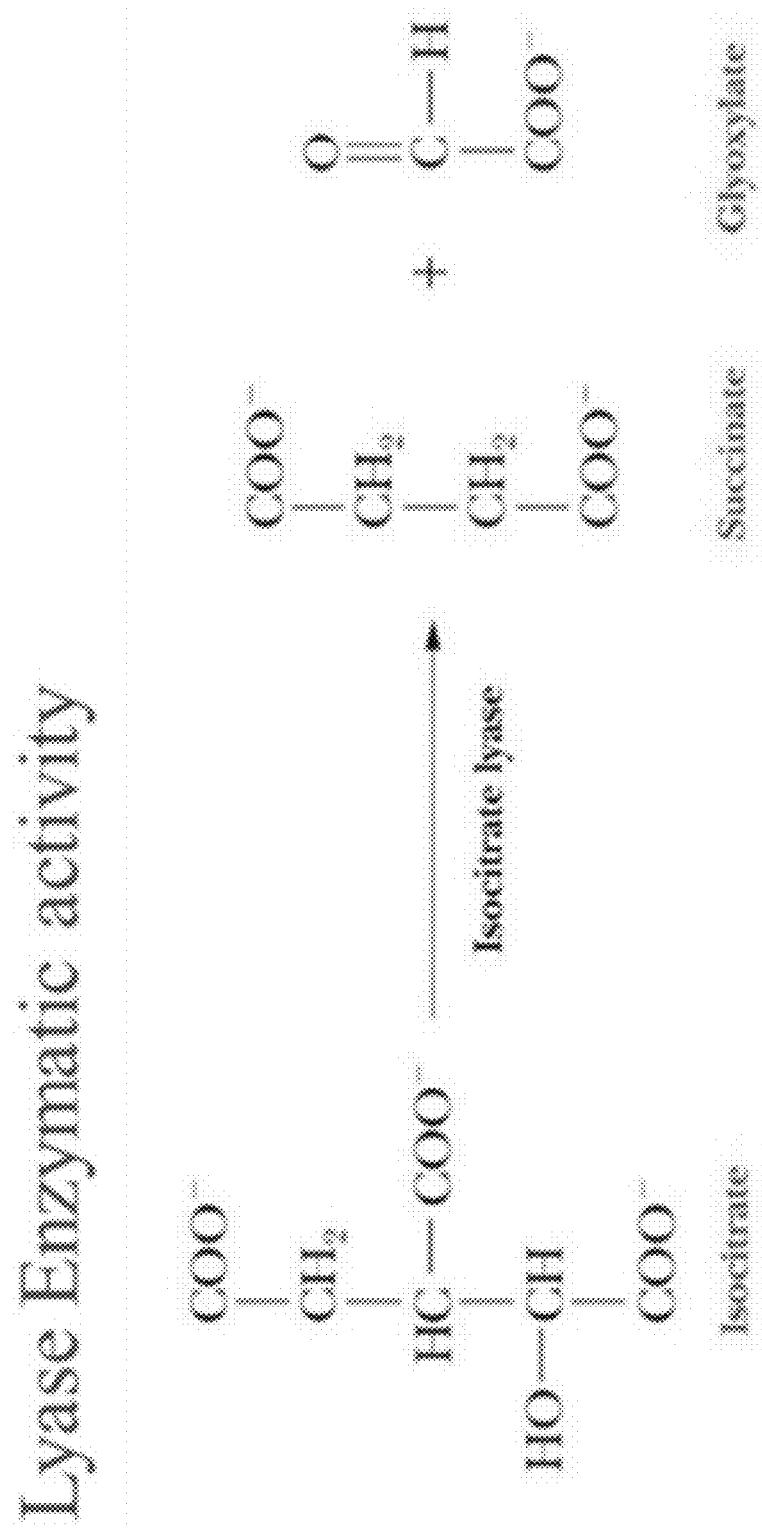
FIG. 13 shows a schematic illustration of non-limiting examples of enzyme reactions where the enzyme activity or interaction or reaction can be detected by sensors, and an example of detection of enzymatic (acetylcholinesterase and protein kinase) activities using electrode sensors and FET sensors
Figure 13:
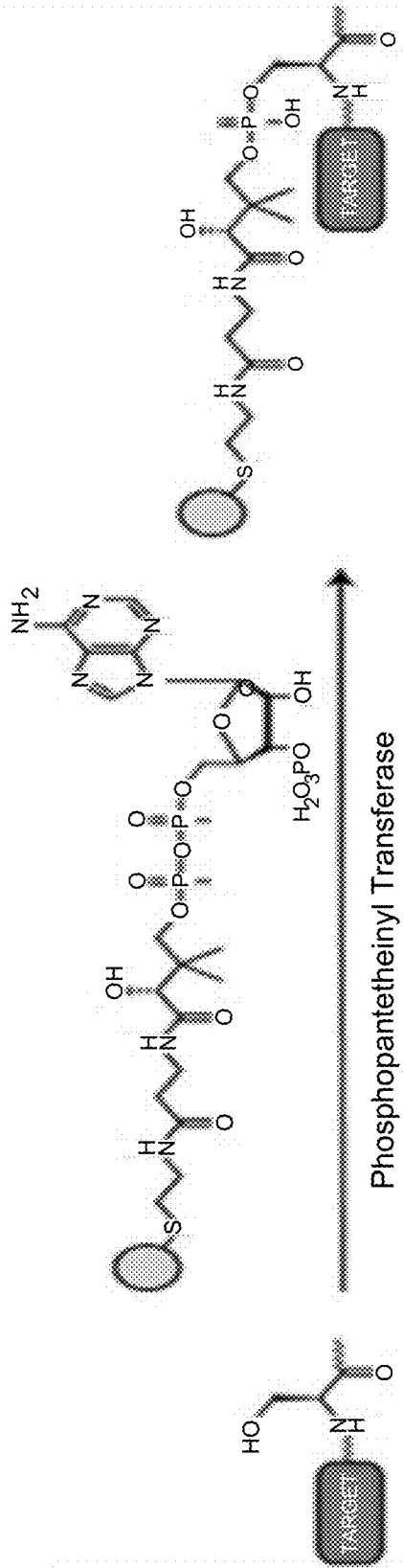
Figure 13:
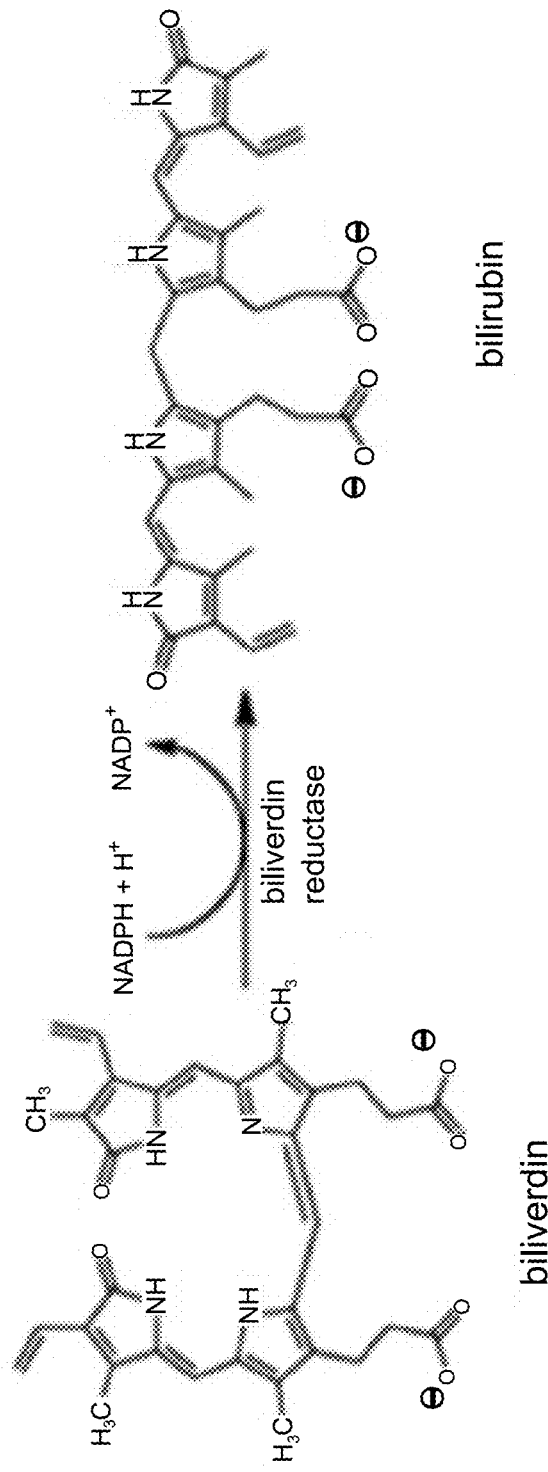
Figure 13:
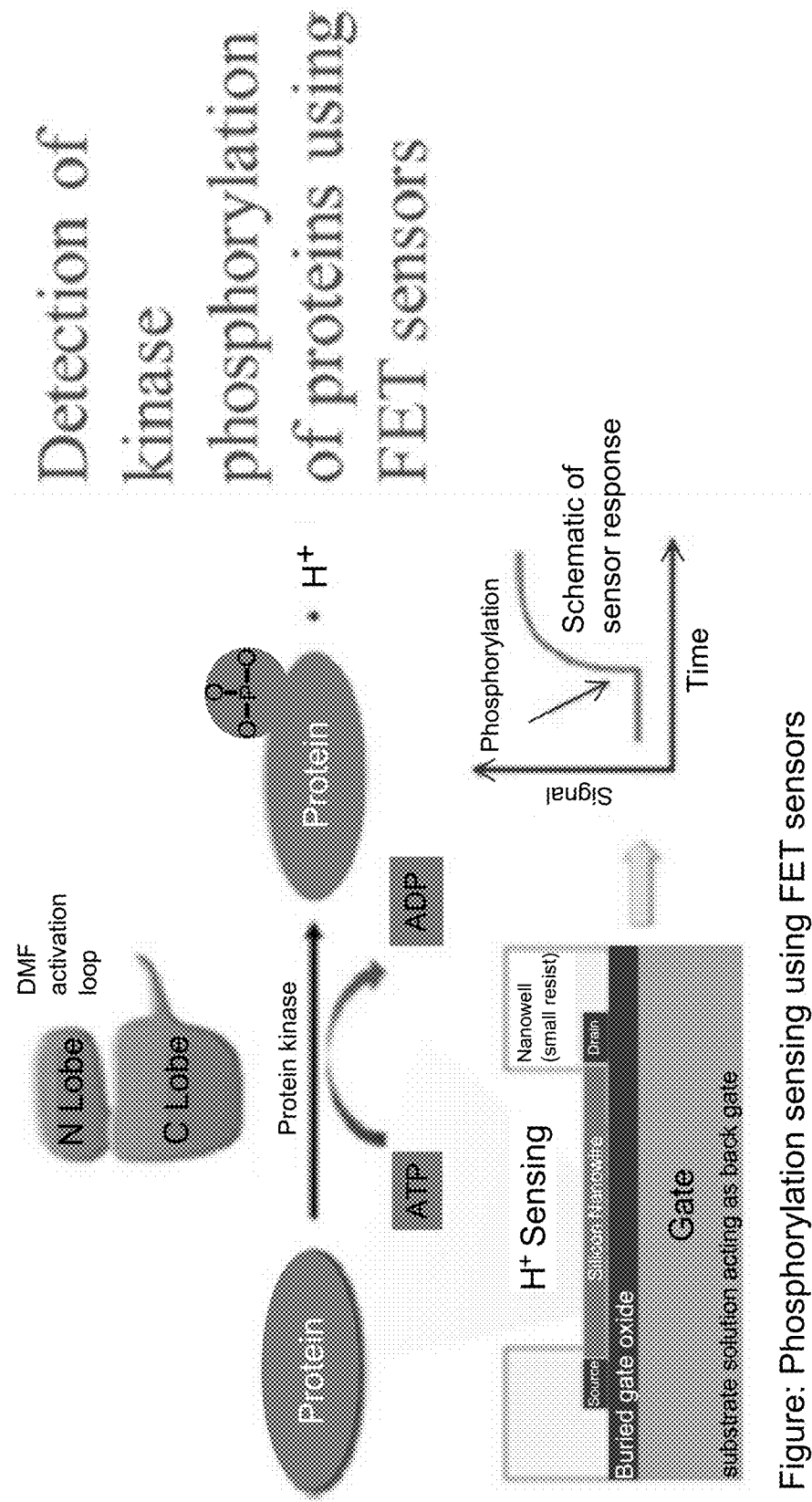

In some embodiments, where the biosensor microarray is configured to detect a reporter agent, it further comprises capture moieties that bind specifically to the reporter agent, e.g., a post-translationally modified protein or peptide, or a proteolytic fragment resulting from interaction between a target ligand in a sample and a reactive polypeptide present in the biosensor microarray. In other embodiments, a biosensor microarray comprises a plurality of sensors that also include a coated layer that is sensitive to the presence of a reporter agent (e.g., a phosphate group moiety, or other ion). See, e.g., FIG. 13 (bottom panel). For example, the sensors can be coated with phospho-affinity agents (Ga(III), Fe(III), Zn(II), and Al(III) metal ion containing films), whereby the phosphorylated product protein is bound to the sensor by the phospho-affinity agent (metal ion) to generate a detectable signal. In some embodiments, the coated layer includes an organic monolayer, a biomolecular monolayer, an inorganic monolayer, a multi layer film, a dielectric film, or a semi-conducting film.

In some embodiments the biosensor microarray comprises an insulator surface such as gold or germanium or alumina surface, to use electro-chemical oxidation-reduction, other electron transport processes to detect and quantify analyte-detector polypeptides indirectly.

In some embodiments the plurality of sensors comprise an array of piezoelectric sensors or acoustic wave sensors (SAW), resonators, cantilever sensors, or electrochemical film coated piezoelectric sensors, such as quartz (QCM), silicon cantilever sensors where variation in frequencies, such as change in resonant frequency, is used to detect interaction with target species In other embodiments, where the biosensor microarray is provided in the form of nanoparticles or beads, the plurality of sensors comprise quantum dots or magnetic particles.

Methods

Generation of Biosensor Microarrays

Any of the biosensor microarrays described herein can be generated by a method that includes the steps of: (i) providing a plurality of capture moieties; linked to a solid support substrate surface, wherein a plurality of sensors are in direct contact or in proximity to the plurality of capture moieties; (ii) providing arrayed in vitro translation reactions comprising RNAs encoding diverse detector (or reactive polypeptides), ribosomes, and diverse detector polypeptides translated from the RNAs; (iii) contacting the arrayed in vitro translation reactions with the plurality of capture moieties, whereby the diverse detector polypeptides bind specifically to the array of capture moieties; and (iv) washing the contacted capture moieties to remove in vitro translation contaminants that are non-specifically bound to the capture moieties, whereby a biosensor microarray substantially free of in vitro translation contaminants is obtained.

In some embodiments the arrayed in vitro translation reactions comprises at least 100 in vitro translation reactions, where each in vitro translation reaction comprises a translated detector polypeptide with a different amino acid sequence from the amino acid sequences of the other translated detector polypeptides. In some embodiments, the arrayed in vitro translation reactions comprise at least 100 to 100,000 in vitro translation reactions (IVTs), e.g., 200 IVTs, 300 IVTs, 400 IVTs, 500 IVTs, 1,000 IVTs, 2,000 IVTs, 3,000 IVTs, 5,0000 IVTs, 7,000 IVTs, 8,000 IVTs, 20,000 IVTs, 30,000 IVTs, 40,000 IVTs, 50,000 IVTs, 60,000 IVTs, 70,000 IVTs, 80,000 IVTs, 90,000 IVTs or another number of IVTs from at least 100 IVTs to about 100,000 IVTs. In other embodiments, the arrayed IVTs comprise at least 3 IVTs to about 50 IVTs e.g., 5 IVTs, 8 IVTs, 10 IVTs, 15 IVTs, 20 IVTs, 30 IVTs, 40 IVTs, or another number of IVTs from at least 3 IVTs to about 50 IVTs.

Figure 3:
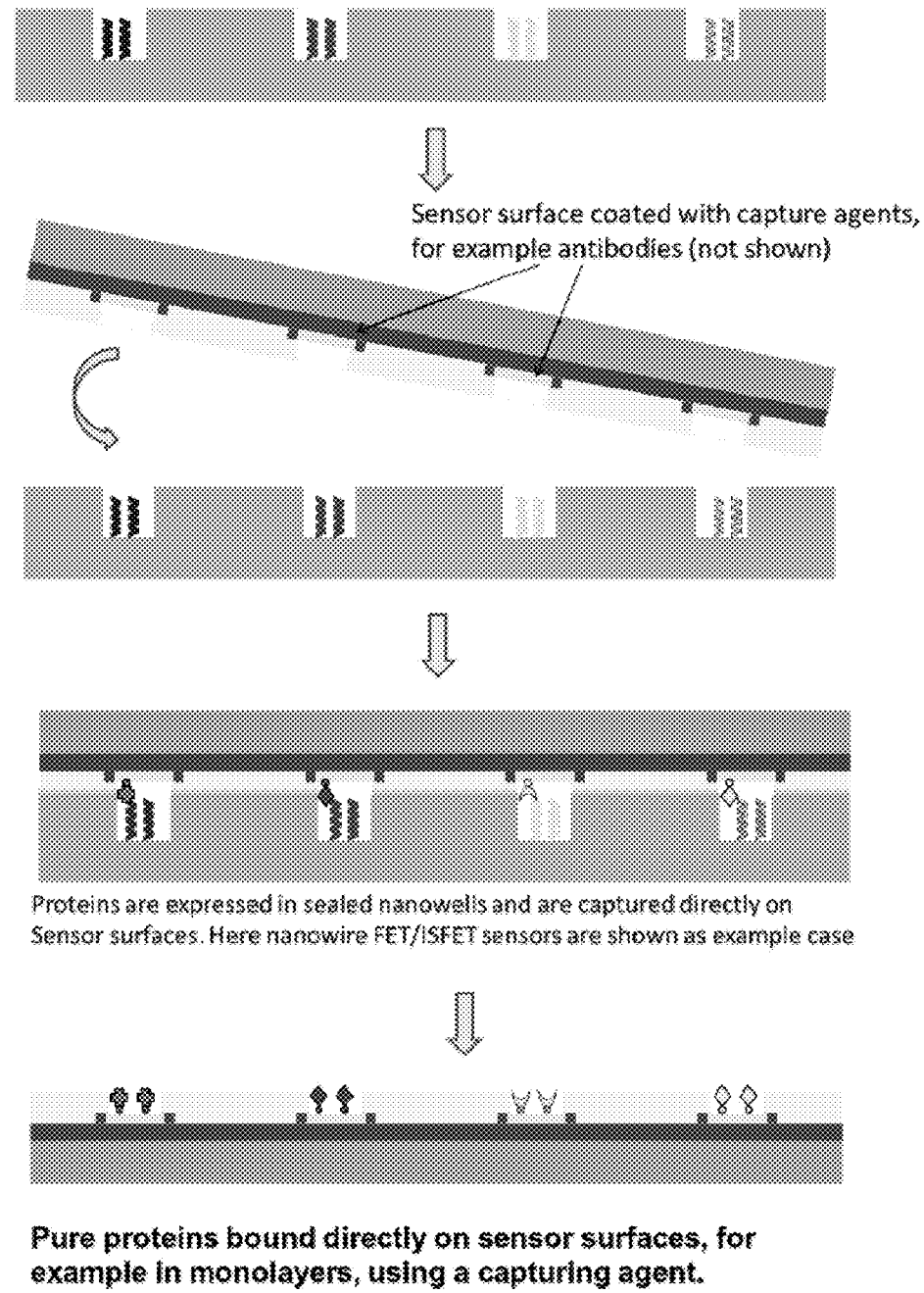
FIG. 3 is a schematic illustration of surface capture protein biosensors. Proteins are expressed in sealed nanowells and captured on a capture agent (e.g. antibody)-coated sensor surface (e.g., in an array format) to generate an array of pure proteins bound directly to the sensor surface by way of a capturing agent (e.g., an antibody). In this, non-limiting embodiment, the sensors are nanowire field effect transistor (FET)/ion-sensitive field effect transistor (ISFET) elements.
Figure 4:
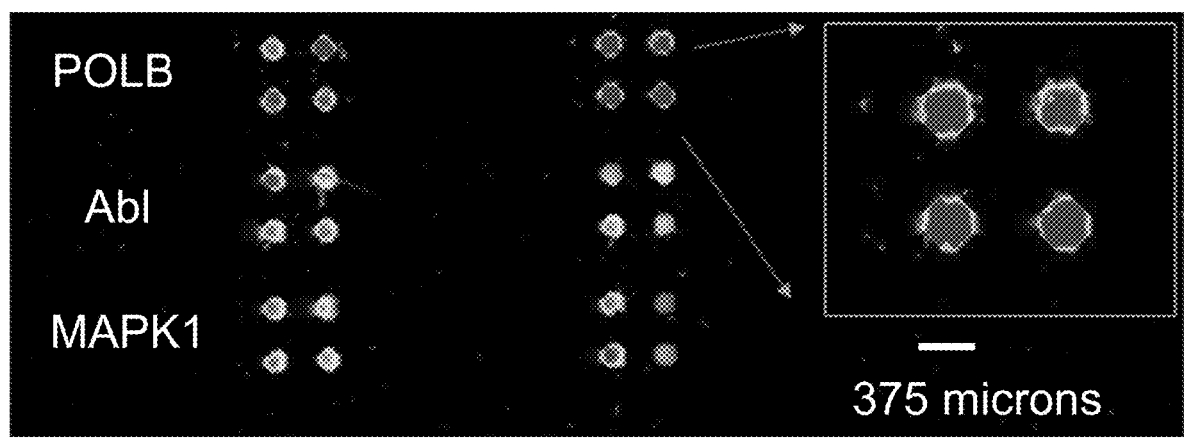
FIG. 4 Isolated capture of pure protein monolayers on glass. POLB, Abl, MAPK1 protein spots are formed by capture on capture moiety coated glass slide. cDNA (plasmids) of POLB, Abl, MAPK1 fusion proteins with GST tags were printed into wells on a silicon nanowells substrate, with well period of 375 microns. cDNA of fusion proteins were printed along with other components of print mixture in groups, in alternate wells. A glass slide coated with anti-GST antibody was used as the capture surface/substrate. Silicon nanowells with cDNA were filled with in-vitro transcription and translation (IVTT) cell extract and the nanowell substrate was capped on the top with anti-GST coated capture glass substrate, and incubated for protein expression. Proteins expressed as fusion proteins with GST tag are captured on the anti-GST coated glass capture surface, which is removed and washed well to yield pure/clean protein arrays on glass slide, with other components of cell extract washed away. The figure shows fluorescent image of pure POLB, Abl, MAPK1 protein arrays in glass slide, with no detectable diffusion or cross contamination of proteins.

Typically, the capture moieties used to generate the biosensor microarrays described herein are provided as a monolayer. In other words, the capture moieties are bound (covalently or non-covalently) to a solid support substrate surface. The capture moiety coated slide is then typically overlayed in contact with an array of isolated in vitro translation reactions (e.g., in microwells or nanowells) to specifically capture in vitro translated proteins (i.e., the detector polypeptides) to form a monolayer of purified detector polypeptides free of contaminants from the in vitro translation reactions (e.g., ribosomes and nucleic acids). See FIGS. 2-4. Detector polypeptides can be generated in array format by any of a number methods known in the art including, but not limited to, nucleic acids programmable protein array (NAPPA), isolated capture or cover capture, protein in situ array (PISA), and DNA array to protein array (DAPA), especially when provided in a nanowell array format. The higher density microarrays reduced the spatial separation of spotted proteins. Experiments with traditional planar slides showed that problems with diffusion of reactants occurred when center-to-center separation distances between spots on the microarray were less than 400 nm. While minimal diffusion was observed at a spacing of 750 nm, significant diffusion was noted when the spot separation was reduced to 375 nm.

In some embodiments in vitro translations are arrayed in sealable nanowells, where each nanowell is about 250 microns in diameter and 75 microns deep with a center to center distance between wells of at least 400 nM to about 1,000 nm. In some embodiments, the in vitro translation arrays are provided in nanowell arrays fabricated on silicon wafers.

See, e.g., Takulapalli et al (2012), *J. Proteome Res.*, (8), pp 4382-4391. Methods for linking capture moieties, e.g., polypeptides such as antibodies or avidin to a metallic substrate surface (e.g., gold) are known in the art as described in, e.g., Moth-Poulsen et al (2010), *Bioconjug Chem*, 21 (6): 1056-1061; Yang et al, (2005), *Langmuir*, 21 (5): 1858-1865.

In some embodiments in vitro translation reactions are provided in arrays of microwells, where a microwell can range in size from about 300 nm in diameter to about 1,000 nm in diameter.

Biosensor Microarray Assays

In various embodiments the biosensor microarrays described herein are used in various applications to detect the presence of one or more analytes in a sample. In various embodiments, a biosensor microarray assay, comprises: (i) contacting a biosensor microarray as described herein with a test sample comprising one or more analytes to be detected, wherein specific binding or interaction or reaction of at least one of the analytes to detector polypeptides or detector peptides in the biosensor microarray generates a detectable signal; and (ii) detecting and determining the signal level associated with binding or interaction or reaction of the at least one analyte with the at least one detector polypeptide or peptide.

In other embodiments, where the biosensor microarray is configured with reactive polypeptides to generate and detect a reporter agent, the method includes the steps of (i) contacting the biosensor microarray of with a test sample comprising one or more target ligands, whereby interaction or reaction of the one or more target ligands with one of the reactive polypeptides generates a reporter agent; and (ii) detecting and determining the signal level of the reporter agent.

Figure 5:
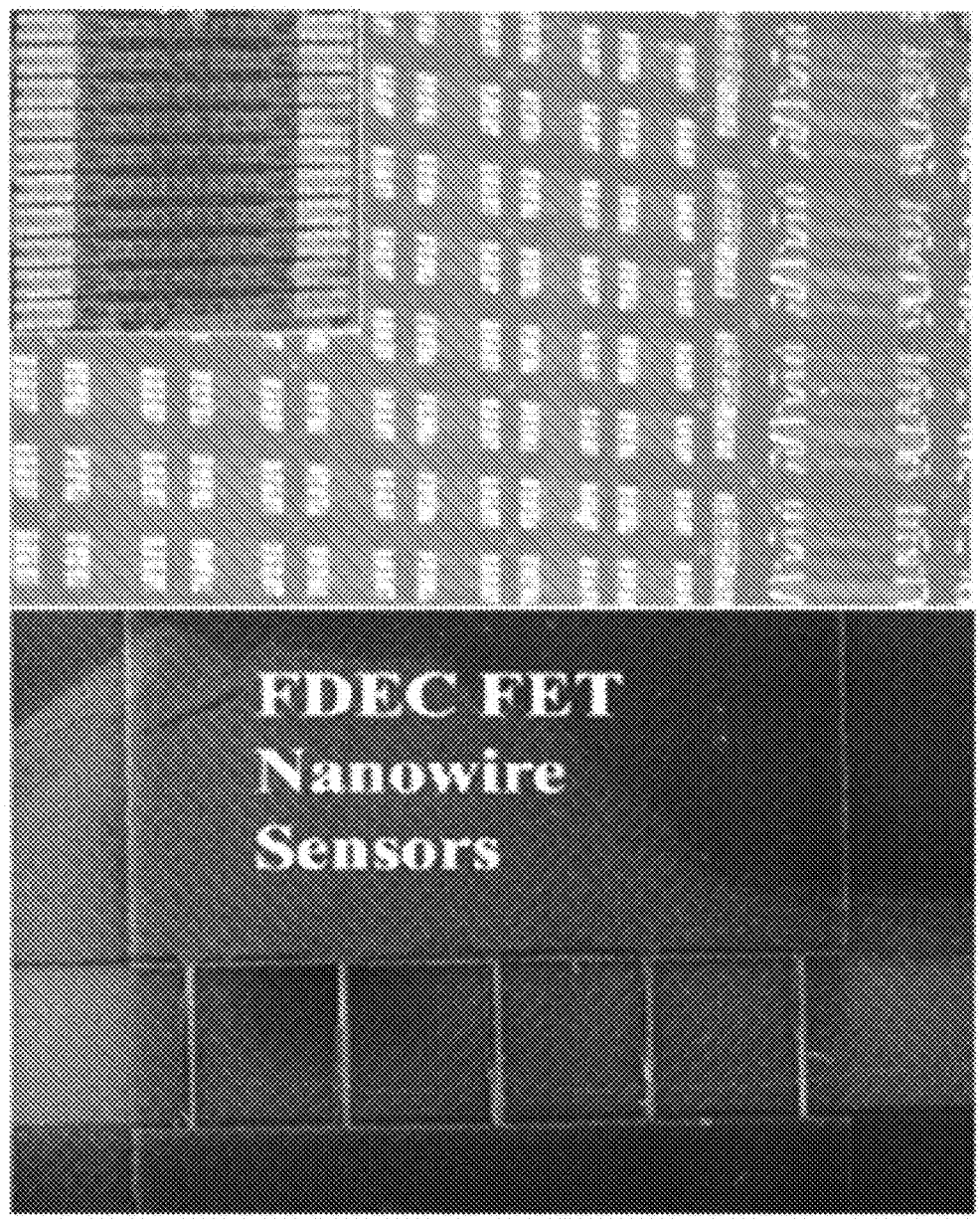
FIG. 5 FET Sensor Array Device Prototype. Top Panel: Optical image of field effect transistor (FET) sensor produced on silicon on insulator wafer substrate, in multiple array designs. In the inset: 10×10 FET sensor arrays with nanowells made in Su-8, including second reference sensor in each array location. Bottom panel: SEM image of FET nanowire sensors.

In some embodiments, the signal is generated by a field effect and transduced via field effect transistor (FET)-based sensors. See, e.g., FIG. 5.

Suitable test samples include, but are not limited to, biological samples (e.g., whole blood, serum, blood fractions, sputum, urine, biopsies, and crude lysates); purified compounds (e.g., small molecule drug candidate compounds); small molecule compound libraries; cell culture protein extracts or spent media supernatant; bacterial cultures; and plant extracts.

In some embodiments, at least 1 to 500 analytes are detected in the sample to be assayed, e.g., at least 1, 2, 4, 5, 7, 10, 15, 20, 30, 50, 75, 100, 150, 200, 300, 400, 450, or another number of analytes to be assayed. In some embodiments, at least ten different analytes are detected in the sample. In some embodiments at least 5000 different analytes are detected in the sample. In some embodiments at least 100,000 different analytes are detected in the sample. In some embodiments at least ten different analytes are detected in the sample.

In some embodiments at least one of the analytes is a protein, an antibody, a non-peptide drug, a metabolite, or a nucleic acid. In some embodiments one or more of the analytes to be detected comprises a drug candidate compound of molecular weight between about 100 daltons and about 900 daltons. For example, where drug candidates are identified by phenotypic screening, a target and or mode of action of the identified drug candidates is unknown. Thus, the biosensor microarrays and microarray assays are very useful for identifying the target (or targets) of drug candidates by detecting the interaction of drug candidates with detector polypeptides in a sensor microarray, or by detecting a byproduct (i.e., a reporter reagent) resulting from such interaction.

Figure 12:
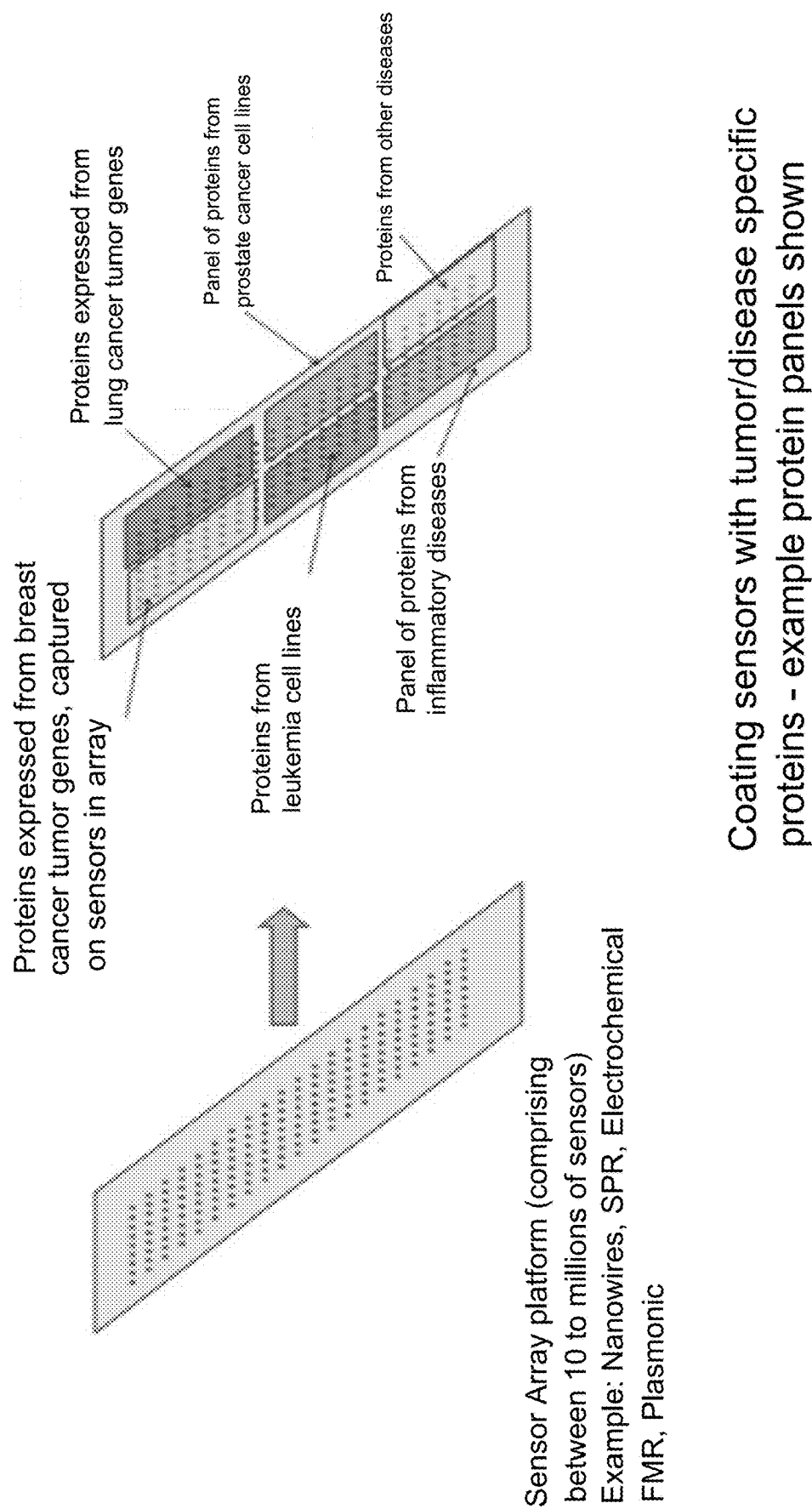
FIG. 12 show a schematic illustration of non-limiting embodiments of a "multiplex" biosensor platform in which sensor arrays are coated with proteins associated with multiple health conditions (e.g., inflammatory diseases, lung cancer tumor proteins, breast cancer tumor genes, leukemia-associated proteins, infection agent proteins, etc.). Testing of patient biological samples for the presence of antibodies to the various arrayed proteins yields an immunoresponse profile to aid in quick disease diagnosis and prognosis.
Figure 12:
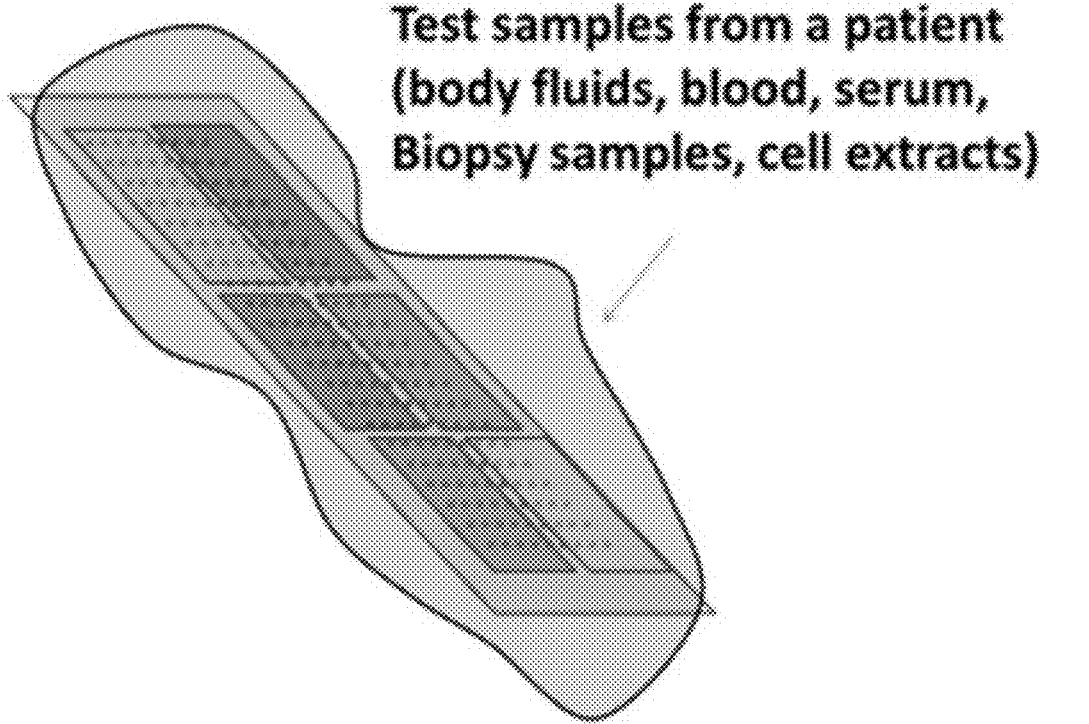

In some embodiments, the analytes to be detected are a plurality of antibodies associated with a health condition (e.g., cancer, an infectious disease, or an autoimmune disease). In effect, the presence of the plurality of antibodies in a biological sample provides a disease-associated diagnostic "signature." See, e.g., FIGS. 11-12.

Figure 6:
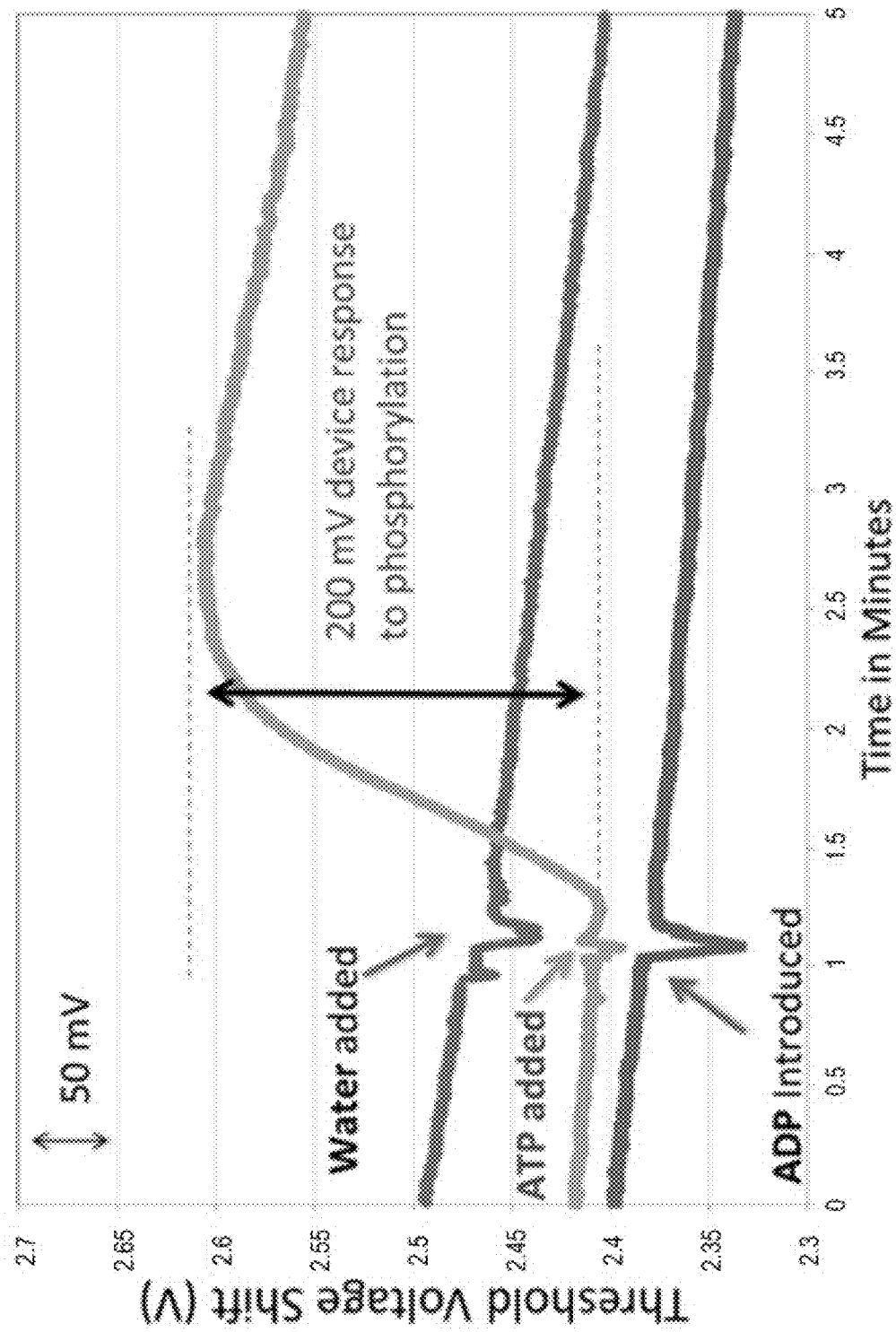
FIG. 6 FET Biosensor detection of phosphokinase activity. This figure shows a fully depleted exponentially coupled (FDEC) response to Src kinase auto-phosphorylation by detecting H$^+$. A 200 mV threshold voltage response is produced upon addition of 10 mM ATP. Addition of pure water or ADP produced no response.
Figure 7:
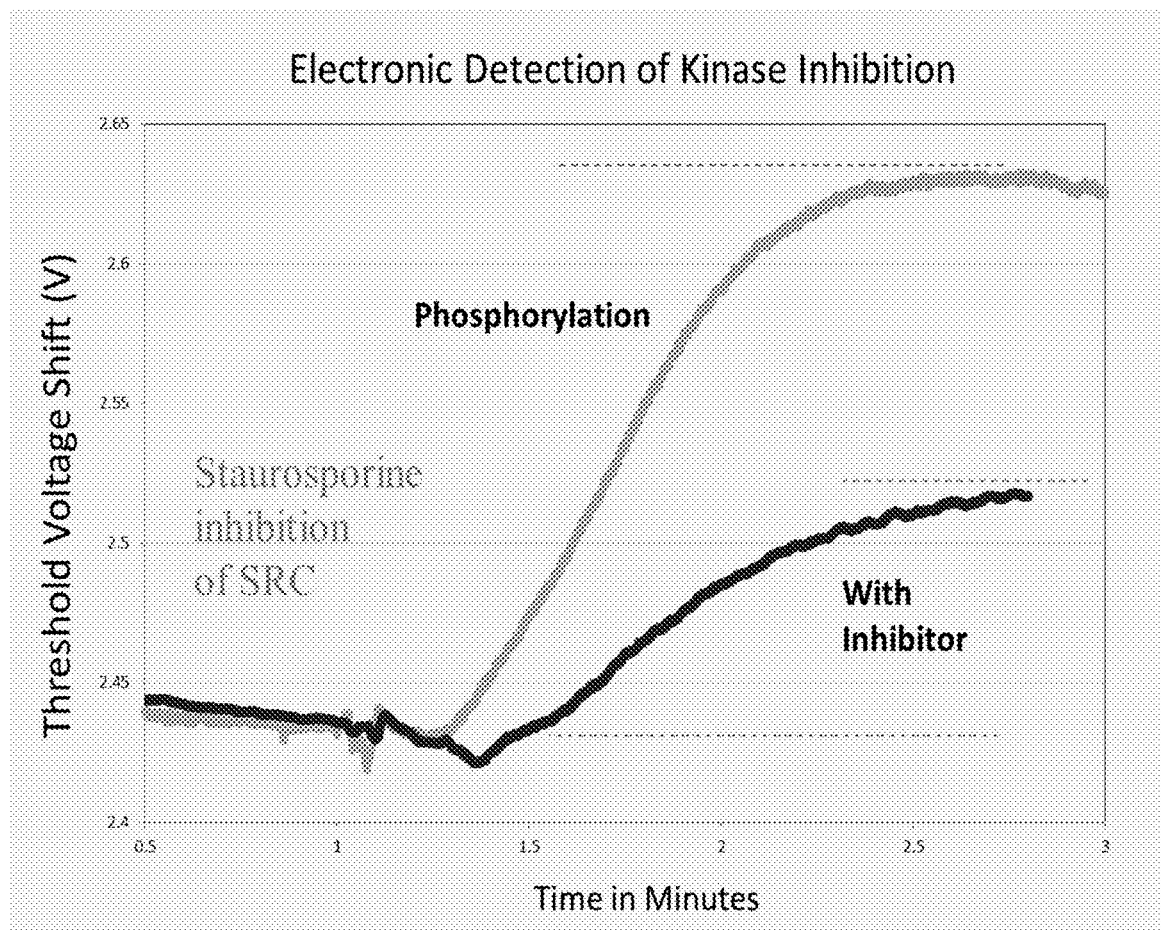
FIG. 7 FET Biosensor detection of Src Kinase inhibition by Staurosporine. shows real time detection of Src kinase autophosphorylation, in the presence or absence of 2 μM staurosporine, using a FET-based biosensor microarray FIG. 8 Schematic illustration of proximity capture protein biosensors. A protein array obtained by isolated protein capture is brought into contact with nanowells containing nanowire sensors and enzymatic substrates. In the presence of a protein, the sensors (e.g., FET/ISFET sensors) detect the presence of a protein reaction (e.g., a converted substrate) or protein-protein interaction.

In some embodiments the biosensor microarray is used to quantify kinetic rates of interaction between one or more analytes in a test sample and the corresponding detector polypeptides. In other embodiments, the biosensor microarray is used to assess inhibition of a protein activity or a protein-protein interaction. For example, where the detector polypeptide is a protein kinase substrate or a kinase with autophosphorylation activity, phosphokinase activity can be detected in the presence or absence of a known or putative inhibitor of the specific phosphokinase activity (see, e.g. FIGS. 6-7). This is also useful for profiling the specificity of a protein kinase inhibitor, where multiple distinct protein kinases are detector polypeptides, their relative activity in the presence and absence of a putative kinase inhibitor can be quantified to determine the specificity of the tested kinase inhibitor compound. Further, where increased kinase phosphorylation is associated with a particular disease state, the kinase activity of particular biological samples can be assessed by contacting a biosensor microarray described herein with the relevant biological sample and detecting phosphorylation of one or more detector polypeptides. Protein kinases are important targets in a number of health condition, e.g., cancer, pulmonary hypertension, diabetes, Alzheimer's, Parkinson's, CNS diseases, macular degeneration, Idiopathic pulmonary fibrosis, systemic sclerosis, rheumatoid disorders, among other diseases, allowing discovery of kinase inhibitor drugs and applying kinase functional screening as disease diagnostics In some embodiments, the biosensor microarray to be used comprises detector or reactive polypeptides that are reversibly bound to the capture moieties as described herein. In embodiments where the detector or reactive polypeptides are reversibly bound, the assay method further includes the step of releasing the reversibly bound polypeptides prior to the detection step. This embodiment is particularly useful where generation of a reporter agent is facilitated by, or requires, interaction of a target ligand with a reactive polypeptide in solution rather than with an immobilized polypeptide, which may cause a steric hindrance. This is also useful when the reporter agent is a post-translationally modified form of the reactive polypeptide itself. For example, the analyte of interest in a sample ("target ligand") may be a protein kinase where the substrate is the "reactive polypeptide" bound to a capture moiety. Release of the reactive polypeptide substrate then allows capture of the phosphorylated by a capture moiety with specific affinity for the phosphorylated polypeptide (i.e., the "reporter agent").

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1 Immunoscreening or Antibody Profiling Using Isolated Protein Capture Sensor Arrays (Prophetic)

An exemplary method of application of protein biosensors disclosed in this application is immune (auto-immune) signature screening or antibody profiling for disease diagnostics and prognostics. Other than antibody profiling, the "disease-ome" and "cancer-ome" biosensors can be used for affinity profiling and interaction profiling (see, e.g., FIG. 12).

For example, genes from tumor cell lines (all genes or specific subset of genes) in breast cancer patients (single patient or multiple patients) can be expressed using a NAPPA-IPC method and resulting tumor proteins/antigens can be captured directly on the device surface (or alternately on secondary surfaces). In this way hundreds to thousands of tumor proteins specific to breast cancer can be produced directly (or in proximity) of sensor devices in an array format. This can be done in a single in-situ expression step, in fairly straightforward fashion, using a library of breast cancer genes. This serves as an excellent diagnostic device for detecting/screening for breast cancer tumors in women in general. If a cancer causing tumor is present in even a very small/initial stage—the body immune system produces antibodies that are specific to these cancerous proteins/biomarkers/biomolecules/cells, and further produced antibodies are in amplified numbers compared to cancer proteins/cells/other cancer biomarkers. Hence sensor devices coated with proteins/antigens expressed from breast cancer genes, as described above, can be used to detect antibodies specific to breast cancer cells in relevant body fluids or biopsy/blood/ tissue specimens from the patient. If an antibody signature (meaning binding pattern of antibodies to breast cancer proteins on sensors), as detected by the underlying sensors, similar to that from breast cancer tumor is observed—then the test patient is indicated to have a high probability of breast cancer tumor. Any of the typical clinical test samples such as blood, serum, biopsy samples, body fluids, saliva, tissue samples, cell lysates, breath extract (exhaled air captured in a solution) etc from test patient can be used in this procedure. By identifying and quantifying the antibody signature the size of tumor and stage of disease can also be detected, because larger numbers of antibodies are present for later stage cancer when compared to early stage cancer. The full breast cancer diagnostic test can be performed in an afternoon, using cancer proteins coated biosensors, where patient antibody signature to library of cancer proteins coated on array of sensors can be used to diagnose presence or absence of breast cancer tumor inside women.

Many current diagnostic tests use detection of protein biomarkers which are often very small in number. However antibody (auto-immune) response to the cancerous proteins/biomolecules/antigens in tissue/cell/body fluid is hugely amplified, where antibodies specific to cancer proteins/biomolecules/cells might be present in orders of magnitude larger numbers than the cancer proteins/biomarkers/cells themselves, aiding easier detection with higher sensitivity. Hence using a simple screen, antibody signature can be obtained to diagnose breast cancer.

Furthermore using such a protein sensor platform, it is possible to detect if a tumor is benign or malignant/cancer causing, its type and sub-type (distinguish between ER+, PR+, HER2+ breast cancers), its drug resistance, stage of development etc. This is because auto-antibody/immune response inside the body is specific to the type and sub-type of disease or cancer inside the body. For example, benign tumors are expected to have different antibody response compared to malignant tumors. So when tested with breast cancer tumor protein sensor library (which may comprise of both proteins from malignant and benign tumor types) the antibody signature or immuno response detected from sensors will be different between the two cases.

Cancer-Ome Protein Sensor Array Chip

By using sensor arrays with large array size, and modifying portions of the array (subset of sensors) with unique sets of proteins expressed from genes of few or all tumors, carcinomas, sarcomas, leukemia, lymphomas—cancer-ome protein sensor chips can be produced that are capable of detecting and diagnosing any of these cancers in a test patient.

Disease-Ome Protein Sensor Array Chip

Using methods described here, protein sensor chip(s) can be produced using panels of proteins specific to a few or all known diseases. This will be useful in detection, diagnosis and prognosis of any and all known diseases and conditions, in test patients.

Detection of Infection

Similar methods can be used to produce sensor array chips modified with proteins/antigens expressed from genes of any or all disease causing pathogens such as virus, bacteria, fungi, Protozoa, helminths, prions, other single and multi-cellular diseasing causing agents. Since immune system of patients who are infected with germs/diseases produces antibodies against germ cells/proteins/lipids etc, profiling of the antibody signature produced specifically in response to the infectious agent will serve as an ideal diagnostic to detect infection in a patient. Protein Biosensors produced by expressing proteins/antigens from pathogens can hence be used to detect antibody response of test patient to detect and diagnose infection, contraction, development of specific diseases. Such sensors can be used in clinic for diagnosing infections and also in biodefense to detect pathogens, bio-agents, chemical-agents, infections etc. In addition to humans, the methods and specific applications described in the disclosure can be used to detect and diagnose diseases, infections and conditions in other animals, other species, wild animals, pet animals, dogs, cats, cows etc.

Example 2 Use of an Antibody Profiling Sensor (Prophetic)

Blood or serum or body fluid or cell extract or tissue extract or biopsy sample of interest, acquired from test patient, will be treated/mixed with magnetic nanoparticles or beads coated with anti-human secondary antibodies (usually used as secondary antibodies, prepared in any host) for a brief period of time. This results in binding of all antibodies present in the test fluid to be captured on to the magnetic particles, which can then be separated out from test fluid in multiple wash steps. Alternately the magnetic beads can be coated with antibody capture agents such as chemical linkers, mix&go coating, bio-conjugates etc. The antibodies captured on the magnetic particles can then be separated/diced/dissociated chemically or enzymatically from the magnetic particles, and the resulting pure antibody solution can be assayed with protein sensor array chips—to detect antibodies specific to the disease, aiding disease diagnosis and prognosis. Alternately magnetic particles with captured antibodies can be directly assayed with protein sensor array chips, and the multiplexed signals from sensor arrays can be used to detect and diagnose diseases and other human conditions.

Example 3 Protein-Protein Interaction Profiling (Prophetic)

Proteome sensor arrays (as described above) can be used for protein interaction profiling, measuring interaction of sensor bound proteins with proteins in patient samples such as blood or serum or body fluid or cell extract or tissue extract or biopsy sample. Proteome biosensor chips are produced by expressing all or a subset of naturally occurring human proteins, including post translational modified proteins. Similar to antibody profiling described above, disease-ome/cancer-ome biosensors can also be used to perform protein—protein interaction profiling by sensing and measuring interaction of proteins in patient samples with sensor bound disease proteins.

Protein—protein interactions are very specific and selective in nature, and hence interaction signature will be unique to diseases, cancers. While DNA interactions are linear in nature to a large extent, protein interactions are multidimensional. Proteins assume multiple roles, at multiple locations and multiple equilibriums, depending on the concentration of protein present at the specific location at the specific instance/time. This is principally because protein functionality is due to their folded three dimensional structures, and protein interactions are equilibrium processes. Thus the challenge in extracting information from complex protein interactions has five dimensions to it: (a) size of information that is extracted (high throughput) (b) 3 dimensional functionality (protein heterogeneity chemically and physically) (c) content or nature of information (can we get kinetic/dynamic information?) (d) fidelity of extracted information (false positives and false negatives?) (e) time (or speed) of information readout (e.g., real time sensing). In addition to solving for protein interaction networks (topologies) that yield information on important aspects such as degree of each node (k), degree-degree correlations, clustering, small-world property, the end goal using the protein biosensors is to understand the kinetics and dynamics of protein interactions in addition to unraveling interaction topologies. The protein interaction signature and interaction topologies extracted from protein biosensor microarrays can be used to acquire a snapshot of all current events occurring in human body, with direct correlation of interactions and rates of interactions with initiation/presence/absence/development of infection or cancer or disease or inflammation or other human conditions etc.

Example 4 Affinity Profiling (Prophetic)

Proteins achieve their functionality by their interactions with other proteins, DNA/oligonucleotides, metabolites, small molecules, antibodies, peptides, ions, signaling molecules and drug molecules. DNA—protein interactions occur through a variety of processes such as electrostatic interactions via salt bridges formation, dipolar interactions via hydrogen bonds formation, hydrophobic/hydrophilic interactions and dispersion forces via base stacking. These differing associations confer sequence specific and protein epitome specific selectivity to these interactions. Understanding protein-DNA interactions, to gain knowledge of nucleic acid sequences that form selective complexes with specific proteins, is central to understanding many cellular regulatory processes such as transcription factor—DNA binding etc. See, e.g., Boon et al (2002), *Nat Biotechnol*, 20(3):282-286 AND Link et al (2013), *Nat Biotechnol* (2013), 31:357-361.

Example 5 Detection of Enzymatic Activity and Post-Translational Modifications (PTM) (Prophetic)

The disclosed protein biosensors can be used to detect enzymatic activity. One examplary application is where at least one enzyme of interest is added to sensor bound protein arrays and specific activity of enzyme against the panel of proteins present is detected via the sensor response. Another exemplary application is where proteins that are bound to array sensor locations are enzymes, where enzyme proteins are produced and captured on sensor locations. These enzyme biosensors can be used to detect specific activity against test proteins, DNA or other biomolecules in the test medium. In both these cases, either the proteins/enzymes are directly bound to sensor surfaces that detect changes to protein/enzymes produced by their reactions, or the protein/enzymes react with target molecules and the reaction products are detected by the sensors. One example biosensors is based on detecting electrons or protons produced by enzyme catalyzed reactions. In another example, products of enzyme catalyzed reaction are detected by biosensors.

In addition protein biosensors described in this application can be used to detect post translational modifications of sensor array bound proteins. Example PTMs that can be detected are, but not limited to, acylation, acetylation, deacetylation, formylation, alkylation, methylation, amidation, glycosylation, oxidation, glycation, phosphorylation, biotinylation, ubiquitination, SUMOylation, Neddylation, sulfation, pegylation, citrullination, dephosphorylation, deamidation, eliminylation.

Example 6 High Throughput Drug Discovery (Prophetic)

Small Molecule or Ligand Interaction Screening

The ability to identify small molecules that interact with proteins, discover ligand molecules to any given protein is of vast importance to understand the protein function, activity regulation and for development of drug molecules. Using strategies such as split-pool synthesis and the development of corresponding tagging technologies it is now possible to prepare large collections of synthetic and natural product-like small molecule compounds. Using protein biosensors described above (proteome biosensors, disease-ome biosensors etc) it is possible to detect small molecule ligands for proteins of interest in a very high throughput fashion. Proteins bound to sensor devices are assayed with small molecules to test specific interactions, by monitoring sensor response. Sensor response will also allow detection of the rate of small molecule/ligand interactions.

The disclosed protein biosensors can be used for toxicology studies, cross reactivity studies where a test drug molecule or a probe molecule such as antibody or small molecule or large molecule is assayed with sensor bound protein arrays to detect cross reactivity from sensors' response. See, e.g., Macbeath et al (1999), *J Am Chem Soc*, 121:7967-7968, which discusses methods of producing small molecule libraries and screening with proteins of interest to detect specific binding or interaction. We disclose the converse of this, where, proteins are bound to sensors in a large array and small molecule binding is detected by measuring the sensor response. See also Wang et al (2005), *Proc Natl Acad Sci USA*, 102(9):3208-3212, which describes detection of small molecule protein interaction using nanowire sensors in the publication.

The following claims are not intended to be limited to the materials and methods, embodiments, and examples described herein.

What is claimed is:

1. A biosensor microarray system comprising:
   (i) a first solid support substrate surface comprising a plurality of nanowells;
   (ii) a plurality of capture moieties linked to a second solid support substrate surface, wherein the second solid support substrate surface is coupled to the first solid support substrate to form sealed nanowells;
   (iii) a plurality of cancer-associated detector polypeptides or detector peptides in the nanowells of the first solid support substrate, wherein the plurality of cancer-associated detector polypeptides or detector peptides specifically bind to the capture moieties on the second solid support substrate surface, thereby forming the biosensor microarray comprising a polypeptide or peptide monolayer on the second solid support substrate surface;
   (iv) a plurality of sensors, wherein the sensors measure changes in electric, resistive, capacitive, inductive, mass, electrochemical, plasmonic, magnetic, optical, or thermal properties of a signal transducing element, or a combination thereof, and
   wherein each sensor in the plurality of sensors is in direct contact with or in proximity at a distance within about 1 millimeter (mm) to the polypeptide or peptide monolayer bound to the plurality of capture moieties.

2. The biosensor microarray system of claim 1, wherein the cancer-associated polypeptides or peptides are human polypeptides.

3. The biosensor microarray system of claim 1, wherein a plurality of cancer-associated detector polypeptides are provided in the nanowells, and wherein the cancer-associated detector polypeptides are selected from tumor antigens, cancer cell line antigens, p53, or a combination thereof.

4. The biosensor microarray system of claim 1, wherein the plurality of sensors generate a detectable signal associated with a binding, an interaction, or a reaction between the cancer-associated detector polypeptides or detector peptides and the plurality of capture moieties.

5. The biosensor microarray system of claim 4, wherein the detectable signal is an antibody signature.

6. The biosensor microarray system of claim 5, wherein plurality of sensors quantify the antibody signature, wherein the antibody signature is indicative of the presence or absence of a cancer health condition.

7. The biosensor microarray system of claim 1, wherein the cancer-associated detector polypeptides or detector peptides are provided by an array of isolated in vitro translation reactions in the sealed nanowells.

8. The biosensor microarray system of claim 1, wherein the plurality of capture moieties comprise antibodies, chemical linkers, affinity agents, or a ligand for a haloalkane dehalogenase tag polypeptide (HaloTag ligand).

9. The biosensor microarray system of claim 1, wherein the plurality of capture moieties comprise proteins, antigens, or a combination thereof, expressed from cancer genes.

10. The biosensor microarray system of claim 1, wherein the cancer-associated detector polypeptides or detector peptides bind reversibly to the capture moieties.

11. The biosensor microarray system of claim 1, wherein the capture moieties comprise non-covalent affinity moieties.

12. The biosensor microarray system of claim 1, wherein the plurality of capture moieties are linked to a plurality of beads or nanoparticles.

13. The biosensor microarray system of claim 1, wherein the cancer-associated detector polypeptides or detector peptides comprise at least 100 different cancer-associated detector polypeptides or detector peptides.

14. The biosensor microarray system of claim 1, wherein the cancer-associated detector polypeptides or detector peptides comprises a post-translational modification.

15. The biosensor microarray system of claim 14, wherein the post-translational modification comprises acylation, acetylation, de-acetylation, formylation, alkylation, methylation, amidation, glycosylation, oxidation, glycation, phosphorylation, biotinylation, ubiquitination, SUMOylation, Neddylation, sulfation, pegylation, citrullination, dephosphorylation, deamidation, or eliminylation.

16. The biosensor microarray system of claim 14, wherein the cancer-associated detector polypeptides or detector peptides comprises at least two polypeptides or peptides comprising the same amino acid sequence, and wherein one of the at least two polypeptides or peptides does not comprise the post-translational modification.

17. The biosensor microarray system of claim 1, wherein the plurality of sensors comprises field effect sensors, piezoelectric sensors, acoustic wave sensors, resonators, plasmonic sensors, SPR sensors, raman sensors, SERS sensors, cantilever sensors, calorimetric sensors, potentiometric sensors, amperometric sensors, conductometric sensors, ion channel sensors, ion sensitive sensors, or impedance spectroscopy-based sensors.

18. The biosensor microarray system of claim 1, wherein multiple sensors in the plurality of sensors are in direct contact with or in proximity at a distance within about 1 millimeter (mm) to each capture moiety in the plurality of capture moieties.

19. A biosensor microarray system comprising:
(i) a first solid support substrate surface comprising a plurality of nanowells;
(ii) a plurality of capture moieties linked to a second solid support substrate surface, wherein the second solid support substrate surface is coupled to the first solid support substrate to form sealed nanowells;
(iii) a plurality of viral polypeptides, bacterial polypeptides, fungal polypeptides, or a combination thereof, in the nanowells of the first solid support substrate, wherein the plurality of viral polypeptides, bacterial polypeptides, fungal polypeptides, or the combination thereof, specifically bind to the capture moieties on the second solid support substrate surface, thereby forming the biosensor microarray comprising a polypeptide or peptide monolayer on the second solid support substrate surface;
(iv) a plurality of sensors, wherein the sensors measure changes in electric, resistive, capacitive, inductive, mass, electrochemical, plasmonic, magnetic, optical, or thermal properties of a signal transducing element, or a combination thereof, and
wherein each sensor in the plurality of sensors is in direct contact with or in proximity at a distance within about 1 millimeter (mm) to the polypeptide or peptide monolayer bound to the plurality of capture moieties.

20. A biosensor microarray system comprising:
(i) a first solid support substrate surface comprising a plurality of nanowells;
(ii) a plurality of capture moieties linked to a second solid support substrate surface, wherein the second solid support substrate surface is coupled to the first solid support substrate to form sealed nanowells;
(iii) a plurality of detector polypeptides or peptides bound to the first solid support substrate, wherein the plurality of detector polypeptides or peptides specifically bind to the capture moieties on the second solid support substrate surface, thereby forming the biosensor microarray comprising a polypeptide or peptide monolayer on the second solid support substrate surface;
(iv) one or more analyte in the sealed nanowell, wherein specific binding, interaction, or reaction of the one or more analyte to at least one detector polypeptide or peptide in the polypeptide or peptide monolayer generates a detectable signal;
(v) a plurality of sensors, wherein the plurality of sensors detect the detectable signal, wherein the sensors measure changes in electric, resistive, capacitive, inductive, mass, electrochemical, plasmonic, magnetic, optical, or thermal properties of a signal transducing element, or a combination thereof, and
wherein each sensor in the plurality of sensors is in direct contact with or in proximity at a distance within about 1 millimeter (mm) to the polypeptide or peptide monolayer bound to the plurality of capture moieties.

* * * * *